(12) United States Patent
Rissman et al.

(10) Patent No.: US 8,376,989 B2
(45) Date of Patent: Feb. 19, 2013

(54) COMPARTMENTED SYRINGE

(75) Inventors: Derek Rissman, Waltham, MA (US);
Jason Fortier, Concord, MA (US);
Arthur Driscoll, Reading, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 12/721,709

(22) Filed: Mar. 11, 2010

(65) Prior Publication Data
US 2010/0249829 A1    Sep. 30, 2010

Related U.S. Application Data

(60) Provisional application No. 61/164,622, filed on Mar. 30, 2009.

(51) Int. Cl.
*A61M 37/00* (2006.01)
*A61M 5/00* (2006.01)
(52) U.S. Cl. ............... 604/89; 604/82; 604/187
(58) Field of Classification Search .............. 606/213; 604/82–92, 187
See application file for complete search history.

(56) References Cited

U.S. PATENT DOCUMENTS

| | | | |
|---|---|---|---|
| 3,494,359 A | 2/1970 | Zackheim | |
| 4,583,978 A * | 4/1986 | Porat et al. | 604/208 |
| 4,735,616 A * | 4/1988 | Eibl et al. | 604/191 |
| 4,898,580 A | 2/1990 | Crowley | |
| 4,915,695 A * | 4/1990 | Koobs | 604/191 |
| 4,995,540 A * | 2/1991 | Colin et al. | 222/132 |
| 5,104,375 A | 4/1992 | Wolf et al. | |
| 5,685,846 A | 11/1997 | Michaels, Jr. | |
| 5,887,755 A | 3/1999 | Hood, III | |
| 5,935,437 A | 8/1999 | Whitmore | |
| 5,971,953 A * | 10/1999 | Bachynsky | 604/90 |
| 6,179,862 B1 | 1/2001 | Sawhney | |
| 6,406,455 B1 | 6/2002 | Willis et al. | |
| 2002/0106310 A1 * | 8/2002 | Zuk, Jr. | 422/102 |
| 2004/0236273 A1 * | 11/2004 | Tanaka et al. | 604/89 |
| 2006/0189944 A1 * | 8/2006 | Campbell et al. | 604/191 |
| 2006/0227653 A1 | 10/2006 | Keller | |
| 2006/0280690 A1 | 12/2006 | Wright et al. | |
| 2007/0005020 A1 | 1/2007 | Laveault | |
| 2009/0062745 A1 * | 3/2009 | Qiu | 604/197 |

OTHER PUBLICATIONS

European Search Report for EP 10250630.0-1269 date of completion is Aug. 25, 2010 (8 pages).

* cited by examiner

*Primary Examiner* — Nicholas Lucchesi
*Assistant Examiner* — Rebecca E Eisenberg

(57) ABSTRACT

A syringe includes a first fluid conduit and a second fluid conduit. The first fluid conduit includes two chambers for accommodating two substances of a plurality of substances. The second fluid conduit is disposed adjacent the first fluid conduit and has a chamber for accommodating one substance of the plurality of substances. The syringe may include a third fluid conduit. Each substance is intermixable to form a discharge material upon advancement of a plunger operably associated with each fluid conduit. The discharge material is defined by the intermixed composition of predetermined volumes of the substances the fluid conduits. The discharge material may be a hydrogel. A connecting tip may be operably associated with each fluid conduit. A syringe may include an end cap disposed on the end of each of the fluid conduits. The end cap may have a venting feature for enabling gas venting while preventing discharge until desired.

23 Claims, 26 Drawing Sheets

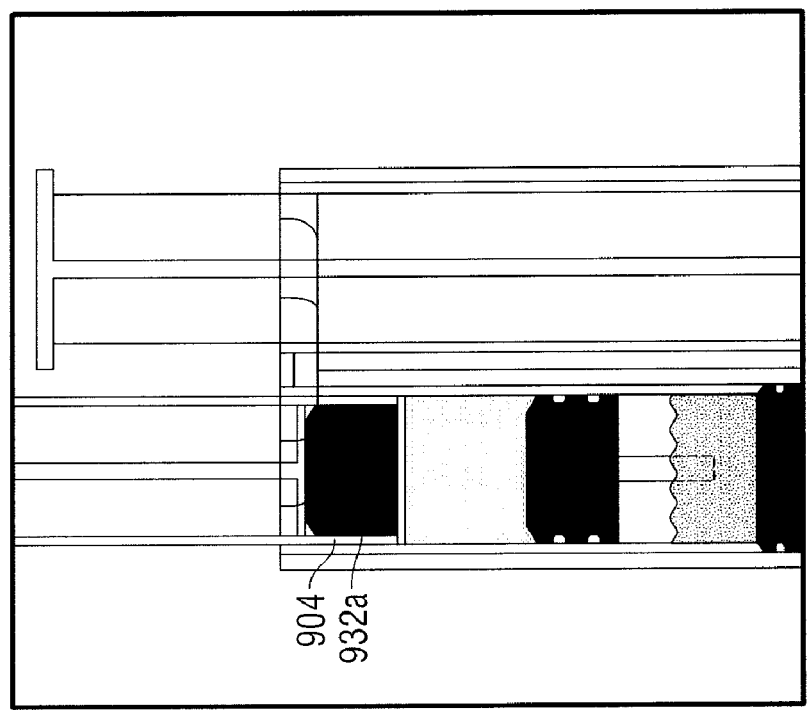
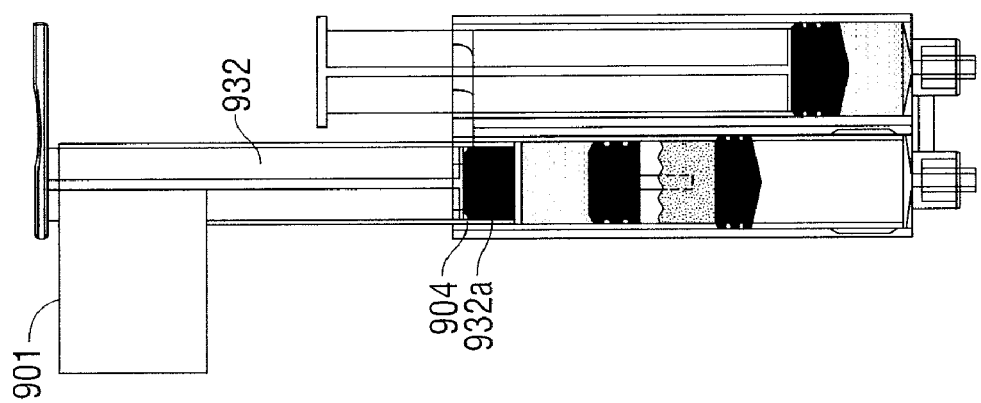

COMPARTMENTED SYRINGE

CROSS-REFERENCE TO RELATED APPLICATIONS

The present application claims the benefit of and priority to U.S. Provisional Patent Application Ser. No. 61/164,622, filed Mar. 30, 2009, the entire contents of which are incorporated herein by this reference.

BACKGROUND

1. Technical Field

The present disclosure relates to applicators, applicator systems, and the like, for mixing two or more substances prior to application.

2. Background of Related Art

Polymers and other synthetic materials are currently being developed for use in internal and external wound closure. "Bioadhesives" are known in the art, as are various methods for applying the bioadhesive. Bioadhesives offer many significant advantages over conventional wound closure methods, i.e., using sutures, staples, clips or other suitable mechanical fasteners. Bioadhesives are faster and simpler to apply, have a tendency to promote quicker wound closure with less scarring, and eliminate the need for a follow up visit to remove the mechanical fasteners.

Most bioadhesives are composed of components that have a tendency to immediately activate and in some instances, rapidly polymerize when combined with one another. Because of this immediate activation and/or rapid polymerization of the bioadhesive, the components comprising the bioadhesive may not be combined until immediately prior to application. Conventional applicators for mixing the bioadhesive components prior to application generally include a mixing chamber or common conduit where the substances are combined, i.e., mixed, as the substances pass therethrough. The consistency of this mixture may vary depending on the types of substances being combined, their quantities, and the speed at which the substances or combinations thereof pass through the mixing chamber.

Conventional applicators or syringes for mixing two substances are known in the art. U.S. Pat. No. 3,767,085 to Cannon et al. discloses such a device. Specifically, the '085 patent discloses a double barrel carpule type syringe for the mixing of an elastomeric base material and an accelerator. The mixing syringe includes, on a distal end thereof, a common mixing and dispensing chamber provided with a rotary agitator driven from a motor on the syringe. The mixing syringe further includes a double plunger through which manual depression thereof results in the discharge of the fluids into the mixing and dispensing chamber.

SUMMARY

Accordingly, the present disclosure is directed to a syringe including a first fluid conduit and a second fluid conduit. The first fluid conduit includes two or more chambers for accommodating two or more substances of a plurality of substances. The syringe includes a bypass for enabling two or more substances of the first fluid conduit to intermix. The second fluid conduit is disposed adjacent the first fluid conduit and has one or more chambers for accommodating one or more substances of the plurality of substances. One or more chambers are hermetically sealed and one or more chambers include one or more internal stoppers for separating two or more substances. One or more of the internal stoppers may be substantially accordion shaped. Each substance is intermixable to form a discharge material for external application upon advancement of a plunger operably associated with its respective fluid conduit. The discharge material is defined by the intermixed composition of predetermined volumes of two or more substances of the fluid conduits.

The first fluid conduit accommodates a liquid substance in a first chamber and a powder substance in a second chamber. The liquid substance and the powder substance are intermixable to form a first fluid conduit substance. The first fluid conduit substance and the one or more substances of the second fluid conduit define the discharge material upon intermixing thereof. The discharge material may be a hydrogel.

The plunger includes first and second members. The plunger may be configured and dimensioned to advance a predetermined volume of two or more of the substances. The first and second members of the plunger may be configured and dimensioned to interlock in order to facilitate the advancement of a predetermined volume of one or more substances and/or the discharge material. The plunger may further comprise one or more flanges disposed at the proximal end for facilitating a user's grip of the plunger. Each of the first and second members of the plunger may be separately advanceable. Alternatively, the first and second members of the plunger may be configured and dimensioned to simultaneously advance. One or more stop mechanisms may be removably coupled to the plunger which prevent the plunger from being advanced distally beyond a predetermined location.

One or more connecting tips may be operably associated with the distal end of one or more of each of the fluid conduits. Each connecting tip is configured and dimensioned to spray the discharge material to a surface disposed externally of the syringe. Each connecting tip may also be configured and dimensioned to accommodate the intermixing of two or more of the substances accommodated by the fluid conduits.

A syringe may include an end cap disposed on the distal end of one or more of each of the fluid conduits. The end cap may have a venting feature for enabling gas venting while preventing substance and/or discharge material discharge until desired.

Another aspect of the present disclosure is directed to a method of mixing comprising the step of: providing a syringe comprising a first fluid conduit having two or more chambers for accommodating at two or more substances of a plurality of substances; and a second fluid conduit disposed adjacent the first fluid conduit and having one or more chambers for accommodating one or more substances of the plurality of substances; each substance being intermixable to form a discharge material for external application upon advancement of a plunger operably associated with each fluid conduit, the discharge material defined by the intermixed composition of predetermined volumes of two or more substances of the fluid conduits. The method of mixing further comprises the steps of: advancing the plunger so that two or more of the substances intermix; shaking the syringe to further facilitate the intermixing of the two or more substances; and discharging the discharge material formed thereby. The method of mixing may further comprise the step of allowing gas to ventilate after the two or more substances intermix.

According to another aspect, a method of assembly includes providing two or more barrels operably coupled with one another. The method includes introducing one or more stoppers into one or more of the two or more barrels such that two or more chambers are formed in one or more of the two or more barrels. The method also includes introducing one or more substances of a plurality of substances in the first chamber of one or more of the two or more barrels and one or more substances of the plurality of substances in the second chamber of one or more of the two or more barrels. One step includes introducing a first plunger in one of the two or more barrels and a second plunger in the other of the two or more barrels. The method further includes positioning the one or more stoppers between a compressed condition and an expanded condition.

BRIEF DESCRIPTION OF THE DRAWINGS

The above and other aspects, features, and advantages of the present disclosure will become more apparent in light of the following detailed description when taken in conjunction with the accompanying drawings in which:

FIGS. 18-27B are progressive views showing a method of assembly.

DETAILED DESCRIPTION OF EMBODIMENTS

Figure 1:
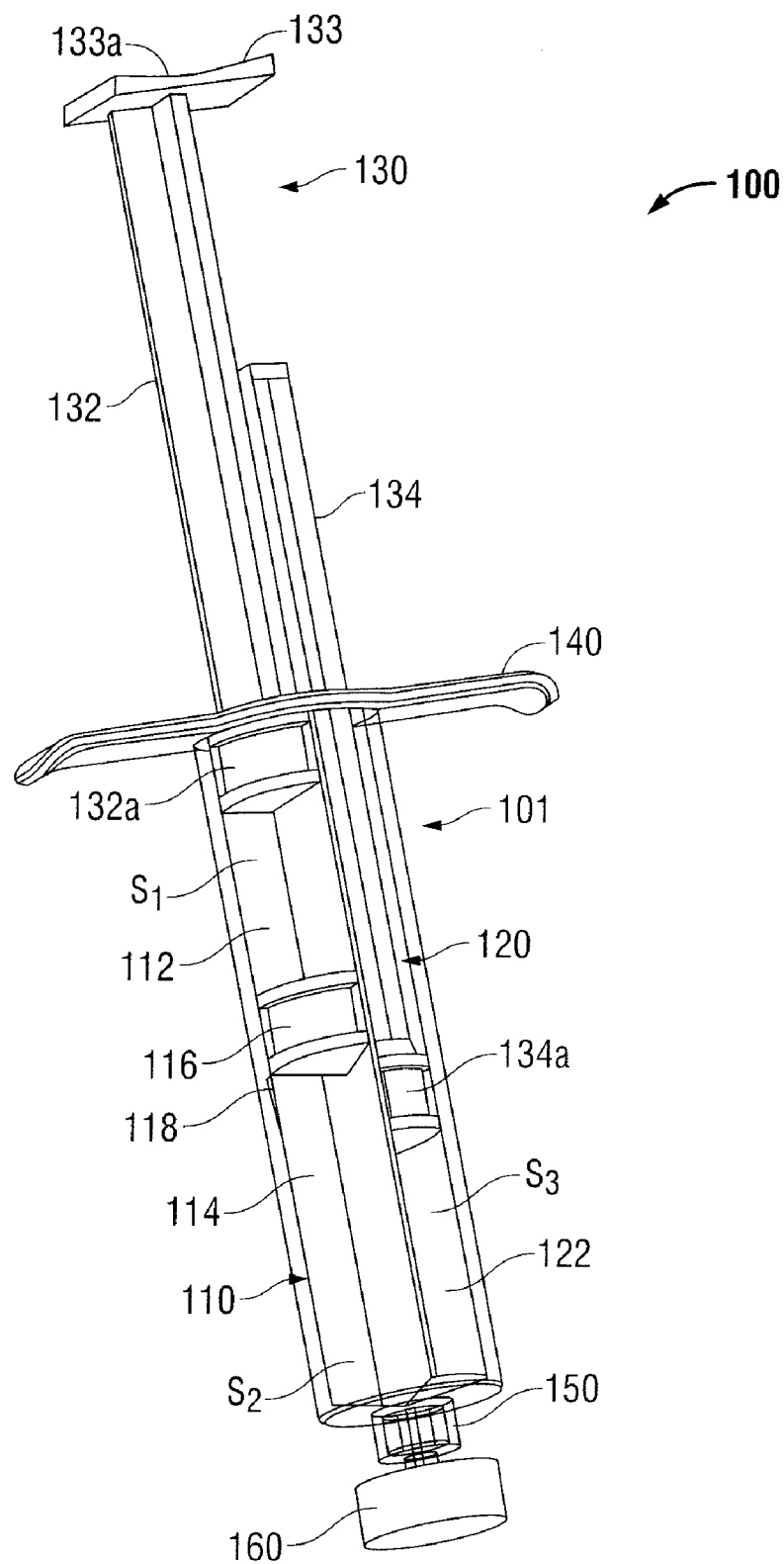
FIG. 1 is a perspective view of one embodiment of a syringe disposed in a first orientation in accordance with the present disclosure.

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

Referring now to the drawings, in which like reference numerals identify identical or substantially similar parts throughout the several views, FIG. 1 illustrates a syringe 100. In accordance with the present disclosure, the syringe 100 includes a unitary barrel 101 having a first fluid conduit 110 and a second fluid conduit 120. The syringe 100 further includes a plunger 130 having a first member 132 and a second member 134. The syringe 100 also includes a finger grip 140, a discharge tip 150, and an end cap 160. The end cap 160 may be replaced with a spray tip ST (FIG. 11) when discharge is desired. The first fluid conduit 110 and the second fluid conduit 120 are disposed within the barrel 101 and are in fluid communication with the discharge tip 150.

With continued reference to FIG. 1, the first fluid conduit 110 includes a first chamber 112 and a second chamber 114 that are separated by an internal stopper 116 and disposed within the barrel 101. The first and second chambers 112, 114 each accommodate one or more substances S1, S2 in a hermetically sealed environment. For example, the first chamber 112 may accommodate a first substance S1, e.g., a fluid precursor (typically a liquid substance), and the second chamber 114 may accommodate a second substance S2, e.g., a polymer (typically a powder substance). The syringe 100 includes a bypass 118 (or may include a plurality of bypasses) for enabling the two or more substances S1, S2 of the first fluid conduit 110 to intermix when the first member 132 of the plunger 130 is depressed or otherwise advanced to a predetermined point. The predetermined point is defined by where the internal stopper 116 exposes a first bypass opening 117 (FIG. 2) of the bypass 118 to enable the first substance S1 to pass through the bypass 118 from the first chamber 112 and out an exposed second bypass opening 119 to the second chamber 114. In other words, the bypass 118 is dimensioned such that the bypass 118 is longer than the internal stopper 116 so that the first and second bypass openings 117, 119 are disposed above and below the internal stopper 116, respectively when the internal stopper 116 is located adjacent the bypass 118. The internal stopper 116 and the bypass 118 are initially disposed at a predetermined distance away from each other, which will be described in greater detail below.

Referring additionally to FIG. 1, the second fluid conduit 120 is disposed adjacent the first fluid conduit 110 within the barrel 101. The second fluid conduit 120 has one or more chambers 122 within the barrel 101 for accommodating one or more substances S3, e.g., a second fluid precursor.

As illustrated in FIG. 1, the first member 132 of the plunger 130 is disposed at the proximal end of the first fluid conduit 110 and the second member 134 is disposed at the proximal end of the second fluid conduit 120 of the barrel 101. The first member has a first member head 132a and the second member 134 has a second member head 134a. The first member 132 is operably associated with the first fluid conduit 110 and the second member 134 is operably associated with the second fluid conduit 120. The first member 132 is shown set off a predetermined distance from the second member 134 in order to facilitate a predetermined volume of substance intermixing within the first fluid conduit 110 prior to engaging the second member 134. For example, the first member 132 may be depressed or otherwise advanced until the first substance S1 readily passes through the bypass 118, enabling the first and second substances S1, S2 to intermix prior to further advancement of either the first or second members 132, 134 of the plunger 130. The first member 132 includes a flange 133 having a thumb pad 133a. The flange is configured and dimensioned to engage the second member 134. The thumb pad 133a is configured for further facilitating a user's grip of the plunger 130. The first and second members 132, 134 of the plunger 130 may be configured and dimensioned to interlock.

In operation, the first member 132 of the plunger 130 is depressed, or otherwise advanced until the applied pressure causes the first substance S1 to advance the internal stopper 116 to a position adjacent the bypass 118 (FIG. 2) such that the flange 133 of the first member 132 engages the proximal end of the second member 134. In this position, a predetermined volume of the first substance S1 may bypass the internal stopper 116 and advance through the bypass 118 such that a predetermined volume of the first substance S1 and a predetermined volume of the second substance S2 of the first fluid conduit 110 may interact. The syringe 100 is then shaken to further facilitate the reconstitution of the first substance S1 and the second substance S2 of the first fluid conduit 110, forming a predetermined volume of a first fluid conduit substance SX (FIG. 3). The end cap 160 is then removed, revealing the discharge tip 150 disposed at the distal end of the barrel 101 that is configured and dimensioned to discharge, e.g., spray (typically with a compatible spray tip ST {FIG. 11} coupled thereto), to a surface disposed externally of the syringe. The discharge tip 150 may be dimensioned for a threaded ISO 594 luer fitting for mating with an existing spray tip ST (FIG. 11) with a standardized luer hook-up. Alternatively, the discharge tip 150 may be dimensioned for a custom luer fitting such that distal end of the discharge tip 150 has wider dimensions for enabling easier distal loading. (However, this requires a custom spray tip with a compatible luer hook-up). It is also contemplated that the different discharge tips may be interchangeable. Upon further simultaneous depression upon each respective member 132, 134 of the plunger 130, the first member 132 causes the first fluid conduit substance SX (FIG. 2) to advance through the first fluid conduit 110 and the second member 134 causes the substance S3 of the second fluid conduit 120 to advance therethrough. Each substance is intermixable to form a discharge material (not shown) for external application upon advancement of the plunger 130 operably associated with each fluid conduit 110, 120. As a result, a discharge material is formed for external application, e.g., through the discharge tip 150 and/or spray tip ST (FIG. 11), from the combination of the substances. The discharge material may be defined by the intermixed composition of predetermined volumes of two or more substances of the fluid conduits 110, 120. The resulting discharge material may be a hydrogel.

Figure 3:
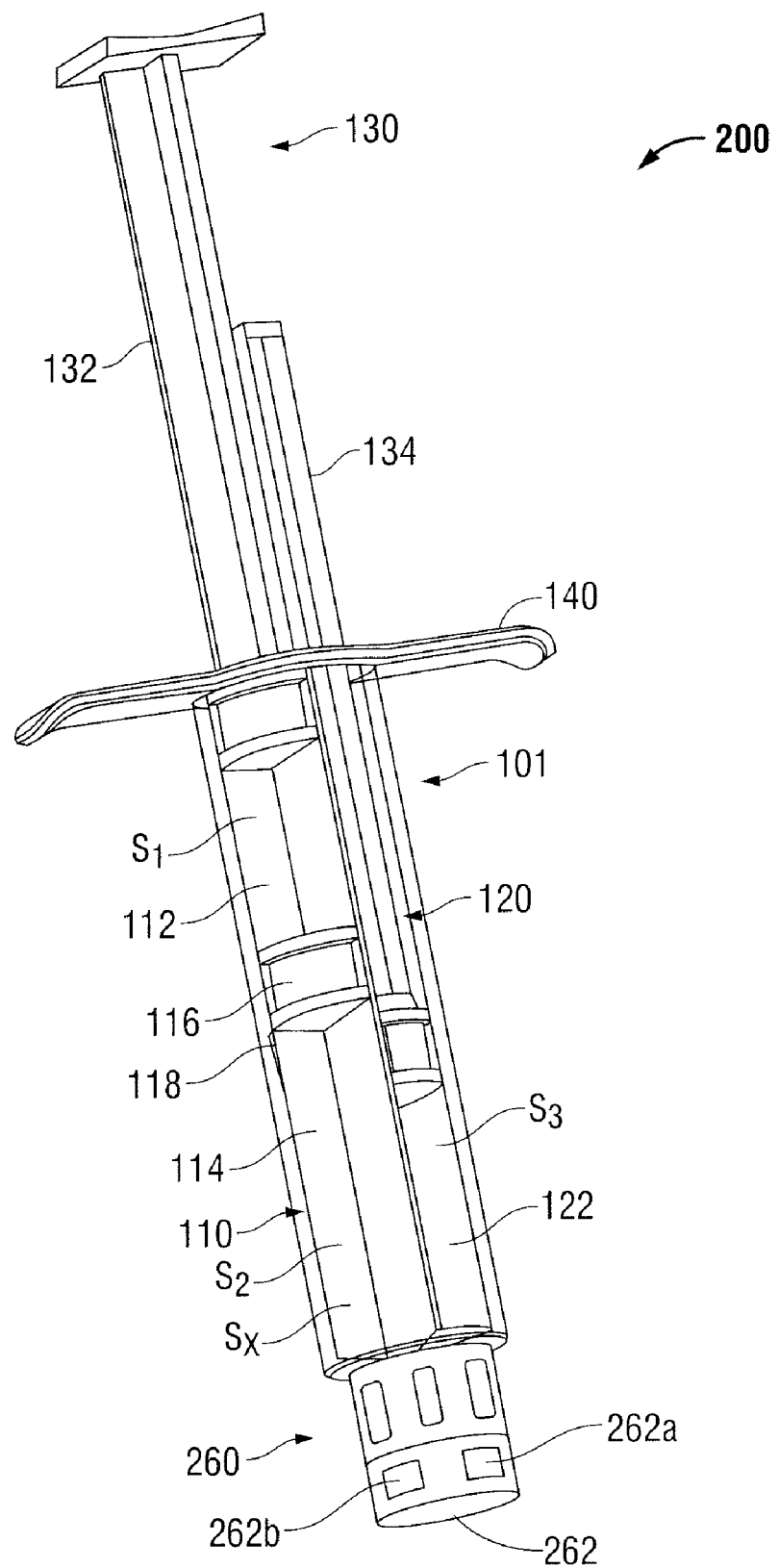
FIG. 3 is a perspective view of another embodiment of a syringe in accordance with the present disclosure.
Figure 4:
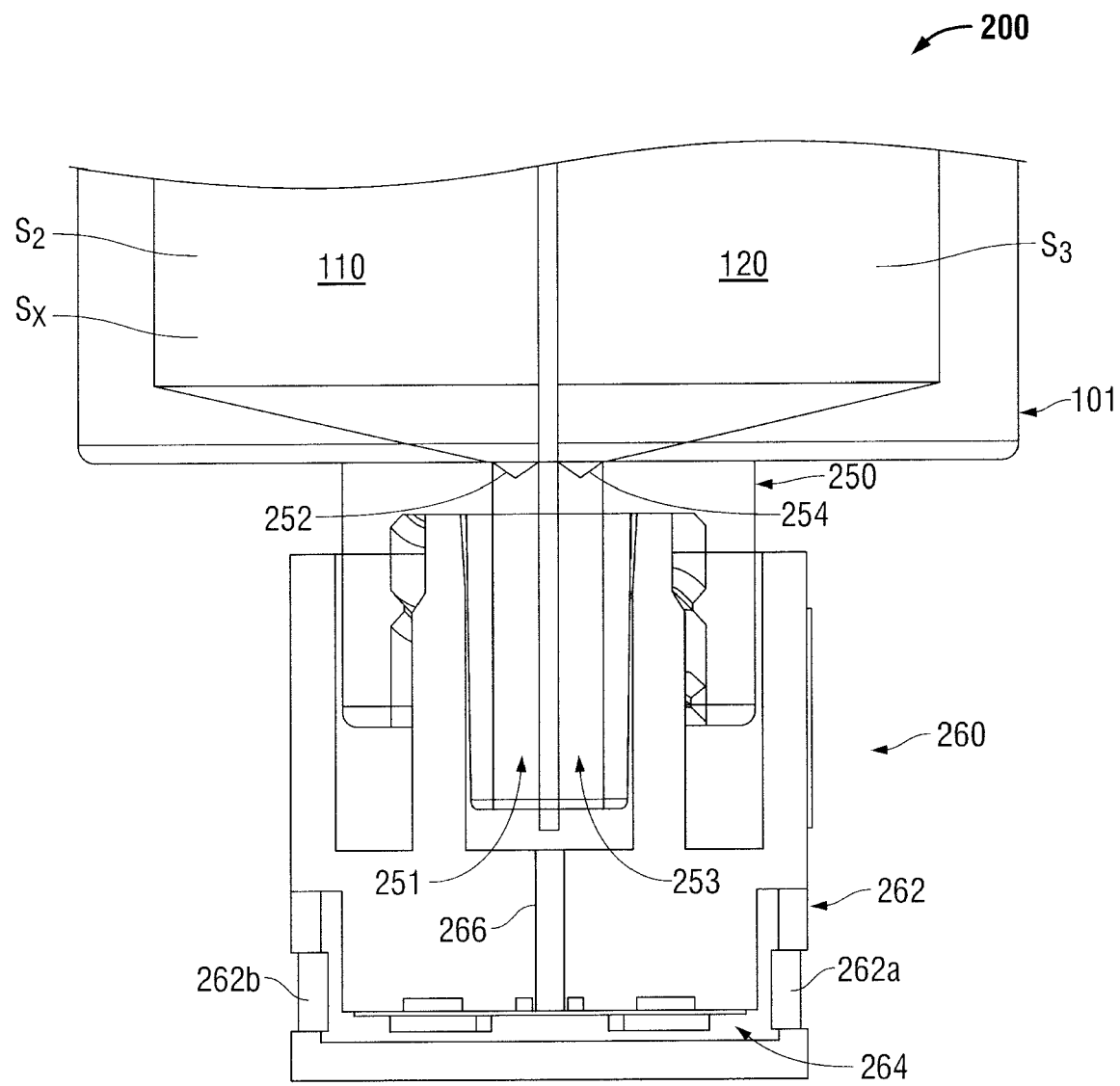
FIG. 4 is an enlarged cross-sectional view of the distal portion of the syringe of FIG. 3.

In one embodiment, shown in FIGS. 3 and 4, a syringe 200 includes a barrel 101 having a first fluid conduit 110 and a second fluid conduit 120 disposed therein. The syringe 200 further includes a plunger 130 having a first member 132 and a second member 134. The syringe 200 further includes a finger grip 140, a discharge tip 250 (FIG. 4), and a vented end cap 260 for providing gas ventilation. The first fluid conduit 110 and the second fluid conduit 120 are disposed in fluid communication with respective first and second channels 251, 253 of the discharge tip 250. The vented end cap 260 is operably associated with the discharge tip 250, by e.g., a luer interface or other like mechanical interface. As shown in FIG. 4, the discharge tip 250 is disposed at the distal end of the barrel 101 and includes a first one-way valve 252 and a second one-way valve 254 disposed at the proximal end thereof. Each one-way valve 252, 254 is disposed in fluid communication with respective fluid conduits 110, 120 and each is configured to prevent any capillary (or similar) effect that would result in premature substance mixing within fluid conduits 110, 120. Each one-way valve 252, 254 enables fluid to pass therethrough when pressure is applied (via plunger members 132 and 134) in each respective fluid conduit 110, 120. The vented end cap 260 includes a venting assembly 262, a filter 264 configured to inhibit fluid from passing therethrough, and one or more passageways 266 configured and dimensioned to facilitate the advancement of fluid therethrough. The filter 264 may have an approximate filtration size of 20 microns which is configured to promote gas venting while inhibiting fluid passage. The venting assembly 262 includes a plurality of vents 262a, 262b, etc. disposed around the perimeter thereof. In order to prevent oxygen and moisture from seeping into the fluid conduits 110, 120 (since the venting end cap 260 is exposed to the atmosphere), the entire syringe 200 may be packaged in an argon back-filled pouch.

Figure 2:
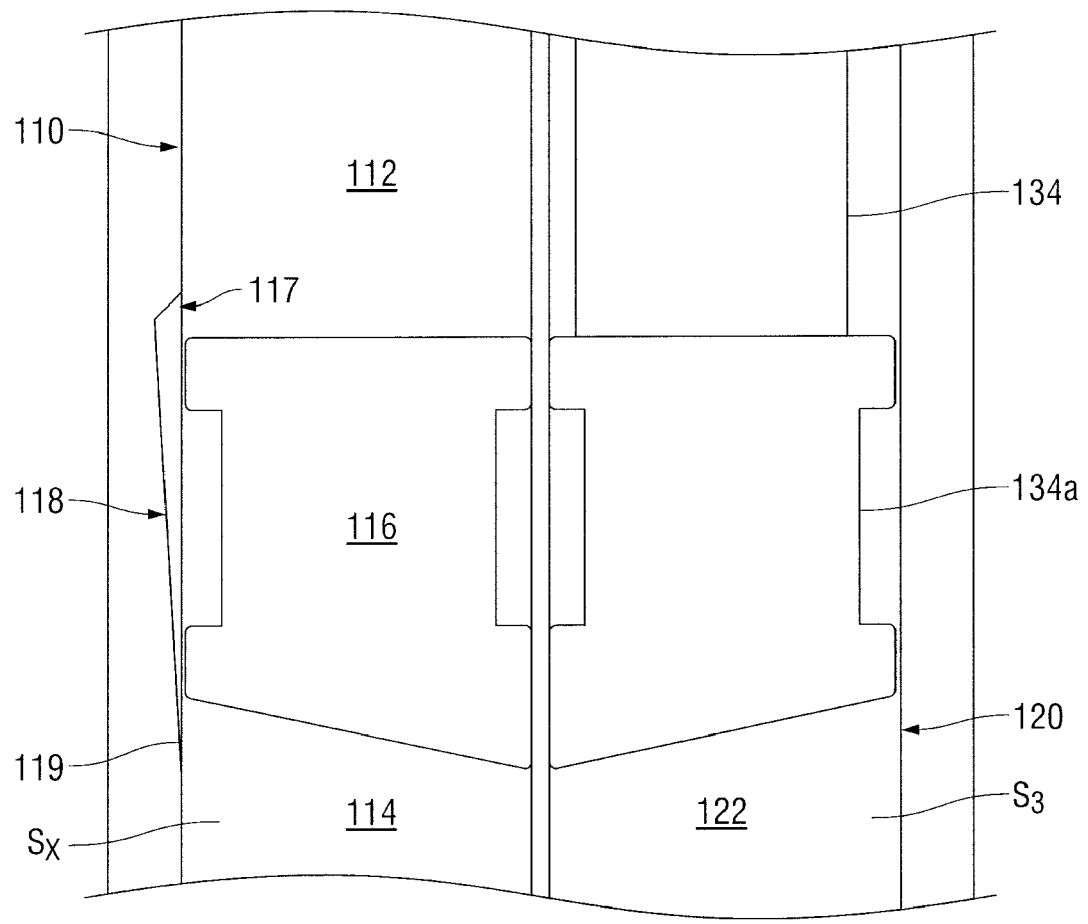
FIG. 2 is an enlarged front cross-sectional view of a portion of the syringe of FIG. 1 disposed in a second orientation.

In operation, this embodiment operates substantially similar to the embodiment illustrated in FIGS. 1 and 2. However, in the embodiment shown in FIGS. 3 and 4, when the first substance S1 intermixes with the second substance S2 of the first conduit 110, the vented end cap 260 will allow for gas ventilation while also preventing substance expulsion. The vented end cap 260 may then be removed and replaced with a spray tip ST (FIG. 11) so that the discharge material may be discharged from the syringe 200.

Figure 5:
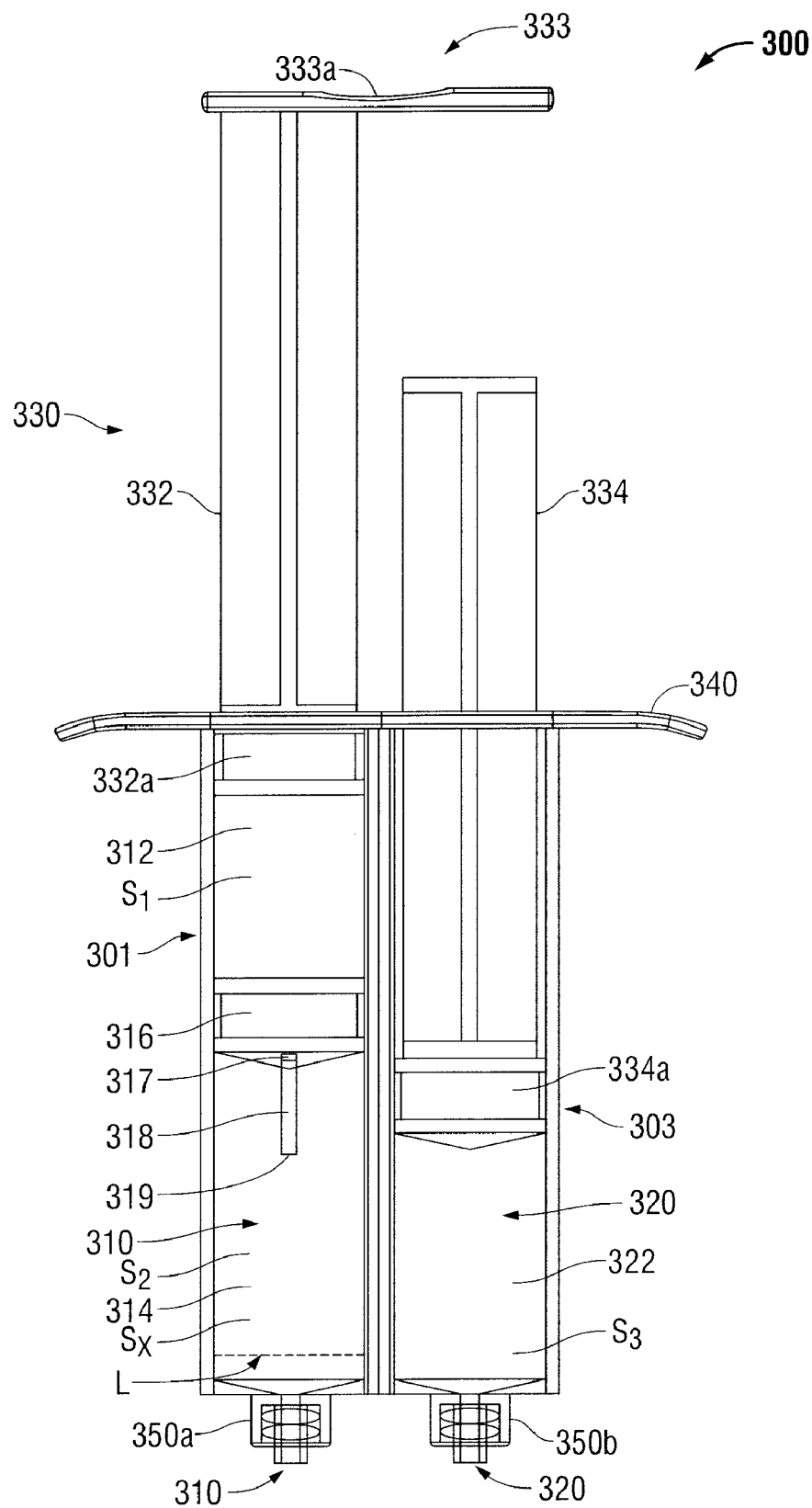
FIG. 5 is a front view of a further embodiment of a syringe in accordance with the present disclosure.

Referring now to FIG. 5, another embodiment of a syringe 300 is illustrated. In this embodiment, the syringe 300 includes a first fluid conduit 310 disposed in a first barrel 301 and in fluid communication with a first discharge tip 350a. The syringe 300 further includes a second fluid conduit 320 disposed in a second barrel 303 and in fluid communication with a second discharge tip 350b. The first discharge tip 350a is disposed at the distal end of the first barrel 301 and the second discharge tip 350b is disposed at the distal end of the second barrel 303. Each discharge tip 350a, 350b may be dimensioned for a threaded ISO 594 luer fitting for mating with an existing spray tip ST (FIG. 11) with a standardized luer hook-up. Alternatively, each discharge tip 350a, 350b may be dimensioned for a custom luer fitting such that the distal end of each discharge tip 350a, 350b has wider dimensions for enabling easier distal loading. (However, this requires a custom spray tip with a compatible luer hook-up). The syringe 300 further includes a plunger 330 having a first member 332 and a second member 334. The syringe 300 also includes a finger grip 340.

With continued reference to FIG. 5, the first fluid conduit 310 includes a first chamber 312 and a second chamber 314, each housed by the first barrel 301. In addition, each chamber 312, 314 is separated by an internal stopper 316. The first and second chambers 312, 314 each accommodate one or more substances S1, S2 in a hermetically sealed environment. For example, the first chamber 312 may accommodate a first substance S1, e.g., a fluid precursor (typically a liquid substance), and the second chamber 314 may accommodate a second substance S2, e.g., a polymer (typically a powder substance). The syringe 300 includes a bypass 318 (but may also include a plurality of bypasses) for enabling the two or more substances S1, S2 of the first fluid conduit 310 to intermix when the first member 332 of the plunger 330 is depressed or otherwise advanced to a predetermined point. The predetermined point is defined by where the internal stopper 316 exposes a first bypass opening 317 of the bypass 318 to enable the first substance S1 to pass through the bypass 318 from the first chamber 312 and out a second bypass opening 319 to the second chamber 314. In other words, the bypass 318 is dimensioned such that the bypass 318 is longer than the internal stopper 116 so that the first and second bypass openings 317, 319 are disposed above and below the internal stopper 316, respectively when the internal stopper 316 is located adjacent the bypass 318. The internal stopper 316 and the bypass 318 are initially disposed at a predetermined distance away from each other. In this embodiment, the bypass 318 is shown disposed on the front of syringe 300. To further facilitate loading of a second substance S2 into the second chamber 314 of the first barrel 301 during manufacturing, the distal end of the first barrel 301 may be configured to removably attach as illustrated by the detaching line "L" of FIG. 5.

Referring additionally to FIG. 5, the second fluid conduit 320 is disposed in the second barrel 303 adjacent the first barrel 301 and has one or more chambers 322 for accommodating one or more substances S3, e.g., a second fluid precursor. Furthermore, the second discharge tip 350b is disposed at the distal end of the second barrel 303.

As illustrated in FIG. 5, the first member 332 of the plunger 330 is disposed at the proximal end of the first fluid conduit 310 (and first barrel 301) and the second member 334 is disposed at the proximal end of the second fluid conduit 320 (and second barrel 303). The first member 332 has a first member head 332a and the second member 334 has a second member head 334a. The first member 332 is operably associated with the first fluid conduit 310 and the second member 334 is operably associated with the second fluid conduit 320. The first member 332 is shown set off a predetermined distance from the second member 334 in order to facilitate a predetermined volume of substance intermixing within the first fluid conduit 310 prior to engaging the second member 334. The first member 332 includes a flange 333 having a thumb pad 333a. The flange 333 is configured and dimensioned to engage the second member 334. The thumb pad 333a is configured for further facilitating a user's grip of the plunger 330. The first and second members 332, 334 of the plunger 330 may be configured and dimensioned to interlock.

In operation, the first member 332 of the plunger 330 is depressed, or otherwise advanced until the applied pressure causes the first substance S1 to advance the internal stopper 316 within the first barrel 301 to a position adjacent the bypass 318 such that the flange 333 of the first member 332 engages the proximal end of the second member 334. In this position, a predetermined volume of the first substance S1 may bypass the internal stopper 316 and advance through the bypass 318 such that a predetermined volume of the first substance S1 and a predetermined volume of the second substance S2 of the first fluid conduit 310 may interact. The syringe 300 is then shaken to further facilitate the reconstitution of the first substance S1 and the second substance S2 of the first fluid conduit 310, forming a predetermined volume of a first fluid conduit substance SX. Upon further simultaneous depression upon each respective member 332, 334 of the plunger 330, the first member 332 causes the first fluid conduit substance SX to advance through the first fluid conduit 310 and the second member 334 causes the one or more substances S3 of the second fluid conduit 320 to advance therethrough. Each substance is intermixable to form a discharge material (not shown) for external application upon advancement of the plunger 330 operably associated with each fluid conduit 320, 330. As a result, a discharge material is formed for external application, e.g., through the discharge tips 350a, 350b, from the combination of the substances. The discharge material may be defined by the intermixed composition of predetermined volumes of two or more substances of the fluid conduits 320, 330. The resulting discharge material may be a hydrogel.

Figure 6:
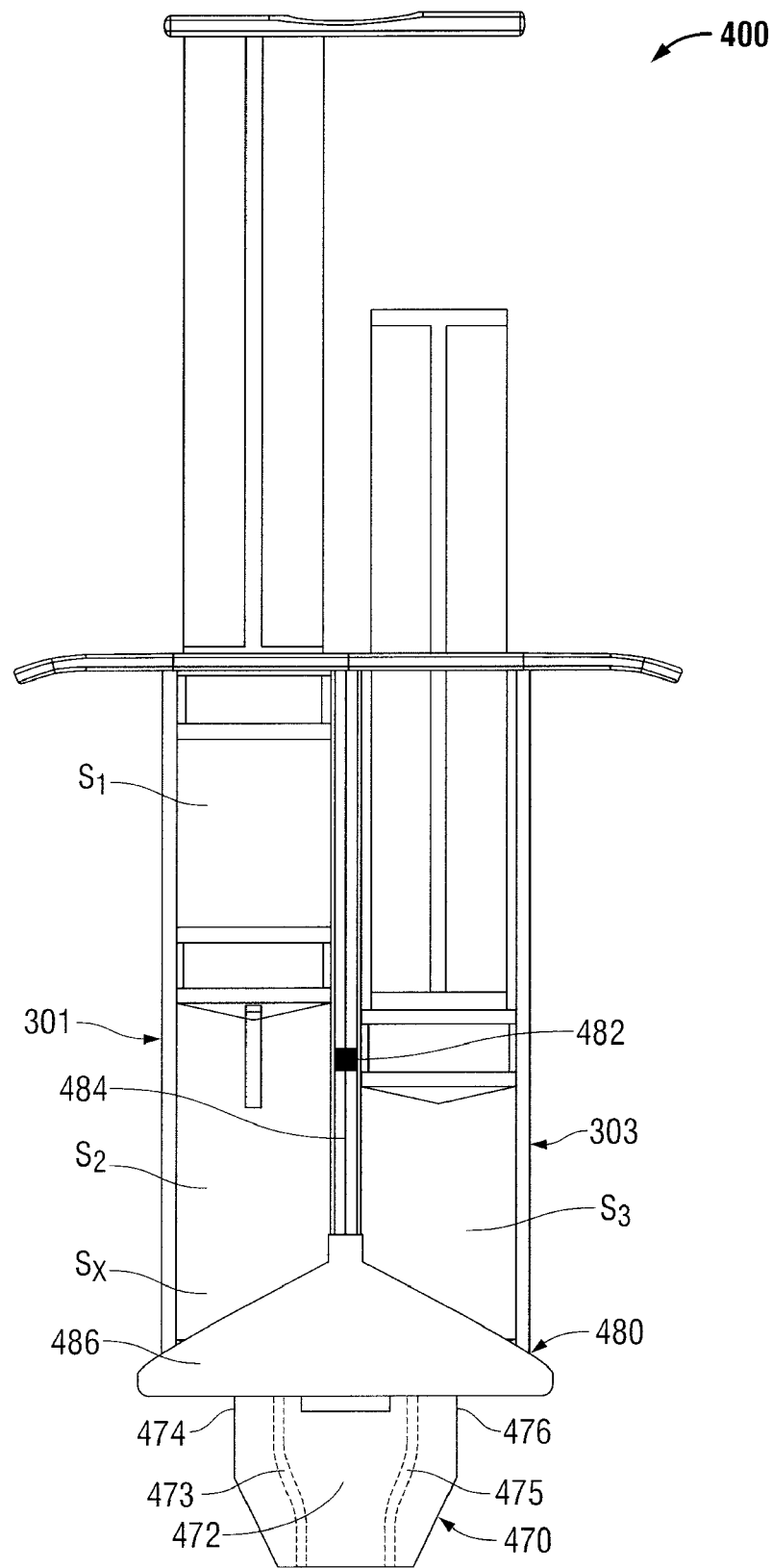
FIG. 6 is a front view of another embodiment of a syringe in accordance with the present disclosure.
Figure 7:
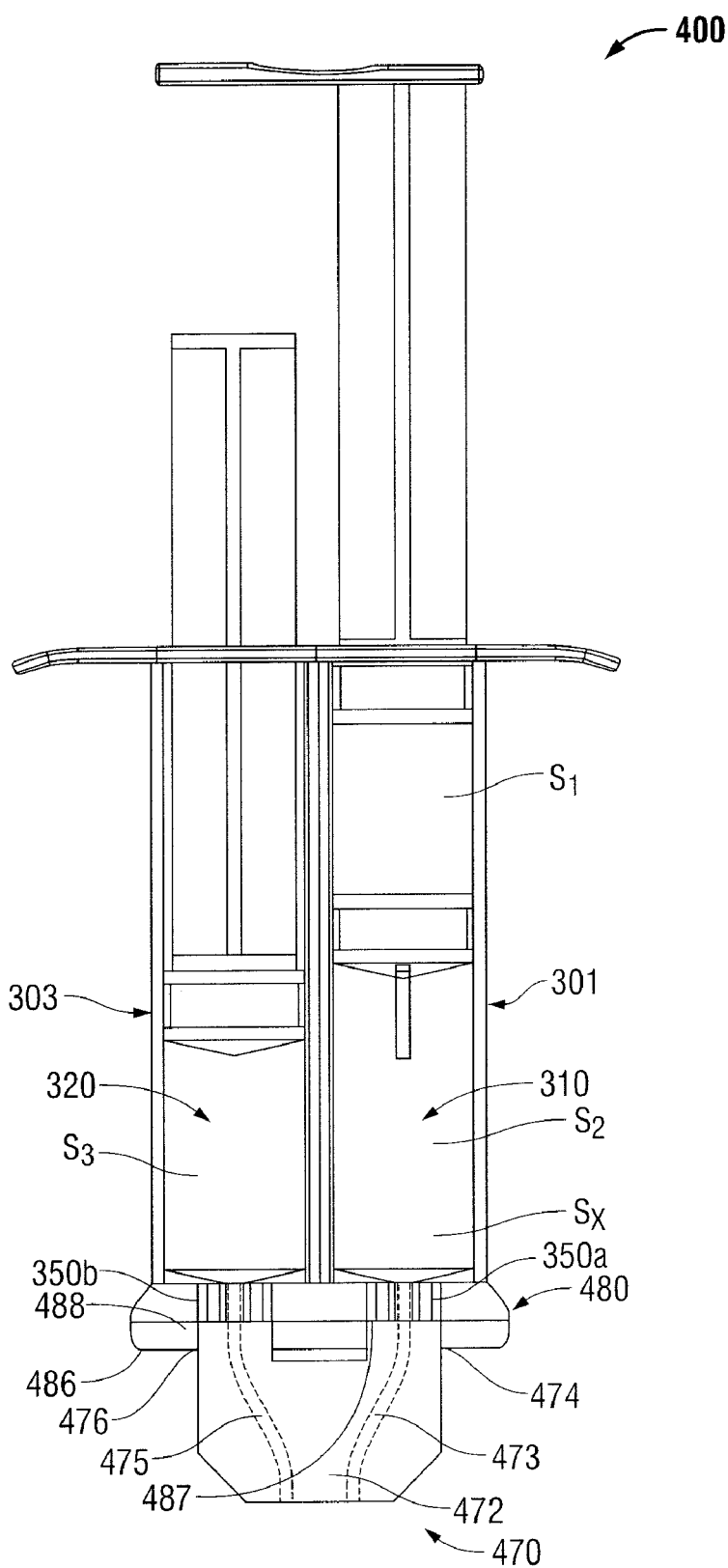
FIG. 7 is a rear view of the syringe of FIG. 6.
Figure 11:
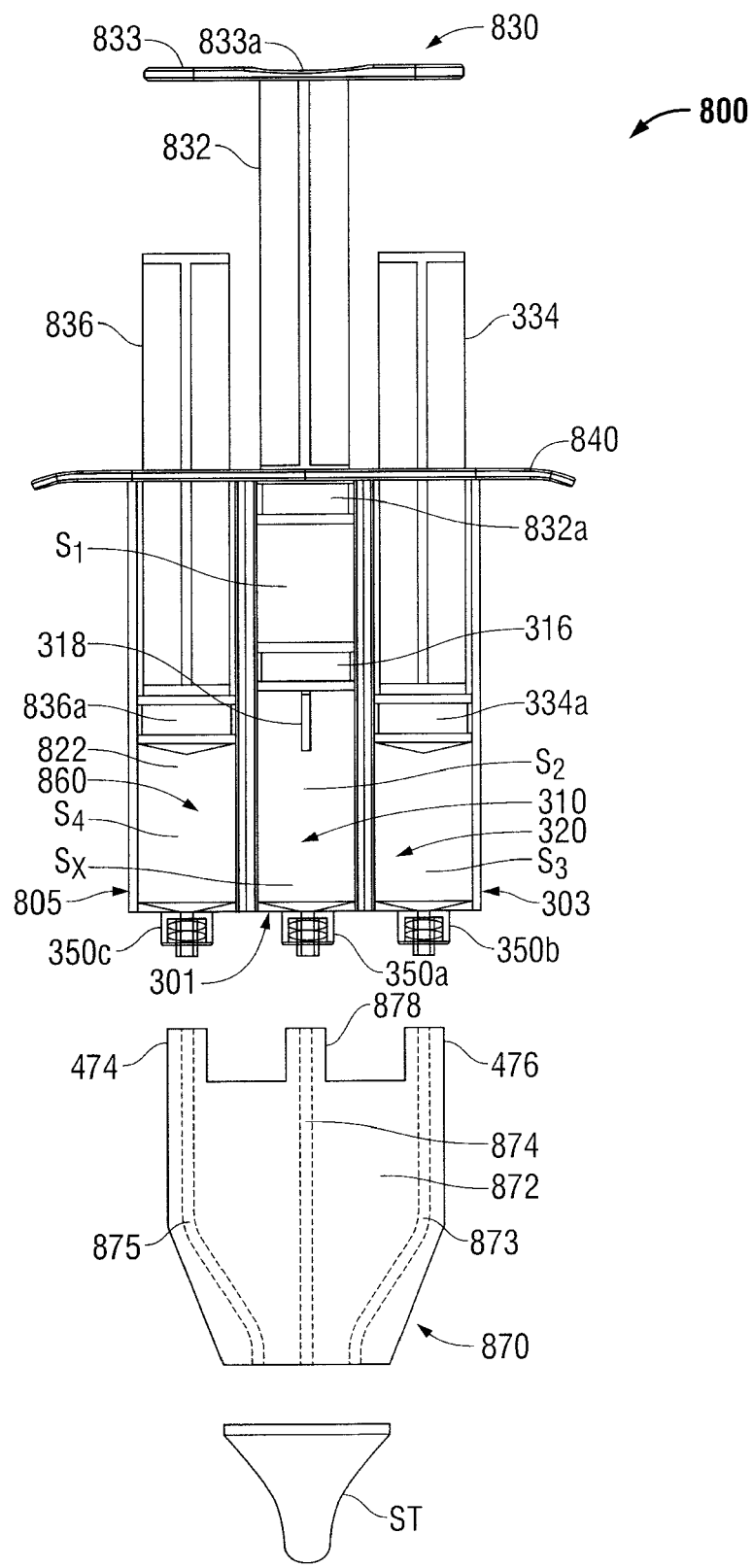
FIG. 11 is a front view, with parts separated, of another embodiment of a syringe in accordance with the present disclosure.

Referring now to FIGS. 6 and 7, another embodiment of a syringe 400 is illustrated. The syringe 400 is substantially similar to the syringe 300, however, the syringe 400 further includes a connecting tip 470 and a latch 480 for removably attaching the connecting tip 470 to the first and second discharge tips 350a, 350b (FIG. 7) of the respective first and second barrels 301, 303. The connecting tip 470 has a body 472 that is substantially y-shaped and may include first and second fluid passages 473, 475 disposed in fluid communication with the respective first and second discharge tips 350a, 350b and the spray tip ST (FIG. 11). However, the connecting tip 470 may also be used as the spray tip (i.e., intermix the substances within the body 472—in which case, the connecting tip is devoid of first and second fluid passages 473, 475 and may be replaceable to prevent clogging). The body 472 includes a first branch 474 and a second branch 476. The first branch 474 is removably attachable to the first discharge tip 350a of the first barrel 301 and the second branch 476 is removably attachable to the second discharge tip 350b of the second barrel 303. As shown in FIG. 6, the latch 480 is rotatably disposed about a pivot 482 and includes a latch arm 484 and a latch head 486. The latch head 486 includes a first coupling feature 487 and a second coupling feature 488 (FIG. 7). The coupling features 487, 488 are configured and dimensioned to couple, (e.g., press-fit or like mechanical engagement) to the respective first and second branches 474, 476 of the body 472 of the connecting tip 470 for removably coupling the connecting tip 470 to the distal ends of the respective first and second barrels 301, 303.

In operation, the syringe 400 operates substantially similar to the syringe 300. In this embodiment, after the reconstitution of substances S1 and S2, the connecting tip 470 may be coupled to the distal end of the first and second discharge tips 350a, 350b. The latch 480 may be rotatably translated until first and second coupling features 487, 488 of the latch head 486 are mechanically engaged with the respective first and second branches 474, 476 of the body 472. After advancing the first and second members 332, 334 of the plunger 330 such that the first fluid conduit substance SX and the one or more substances S3 of the second fluid conduit 320 advance from the respective discharge tips 350a, 350b, the first fluid conduit substance SX and the one or more substances S3 of the second fluid conduit 320 pass through the body 472 of the connecting tip 470 and discharge out the distal end, typically, through an attached spray tip ST (FIG. 11). The resulting discharge material may be a hydrogel.

Figure 8:
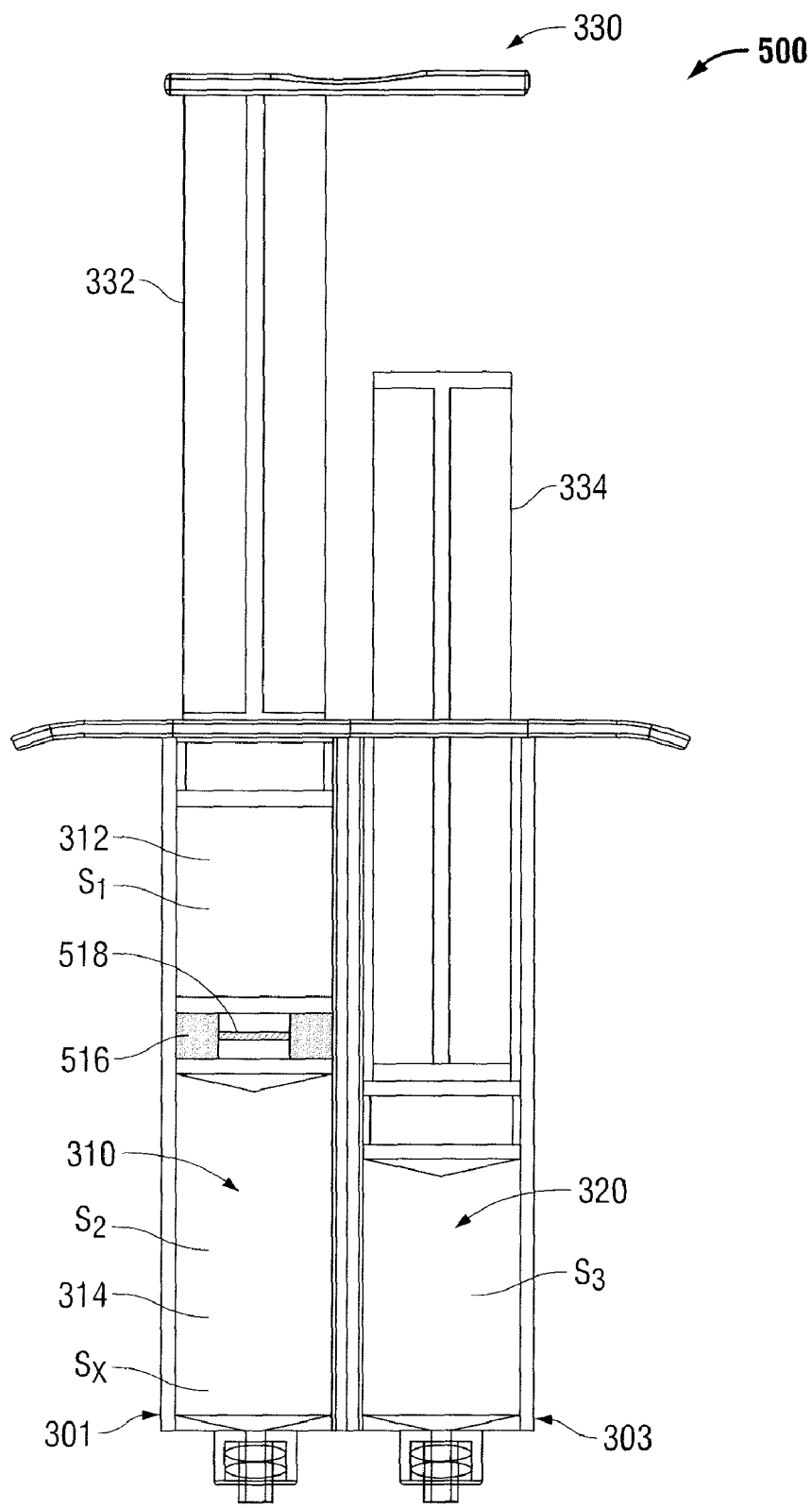
FIG. 8 is a front view of one embodiment of a syringe illustrating an internal stopper and a bypass in cross-section.

Shown in FIG. 8 is a syringe 500 that is substantially similar to syringes 100, 200, 300, and 400. However, syringe 500 includes an internal stopper 516 having a bypass 518 centrally disposed therein. In this embodiment, the bypass 518 is a pressure filtration membrane 518 disposed in mechanical cooperation with the internal stopper 516 about the longitudinal axis thereof. In operation, the first member 332 of the plunger 330 is depressed, or otherwise advanced until applied pressure causes the membrane 518 to rupture, allowing the first substance S1 to advance through the membrane 518 and into the second chamber 314 of the first fluid conduit 310 before the internal stopper 516 is advanced, leaving no particulate. Although this embodiment is illustrated in a double barrel configuration, it is within the scope of the present disclosure that the pressure filtration membrane may also be configured for use in a single barrel configuration or other multiple barrel configurations.

Figure 9:
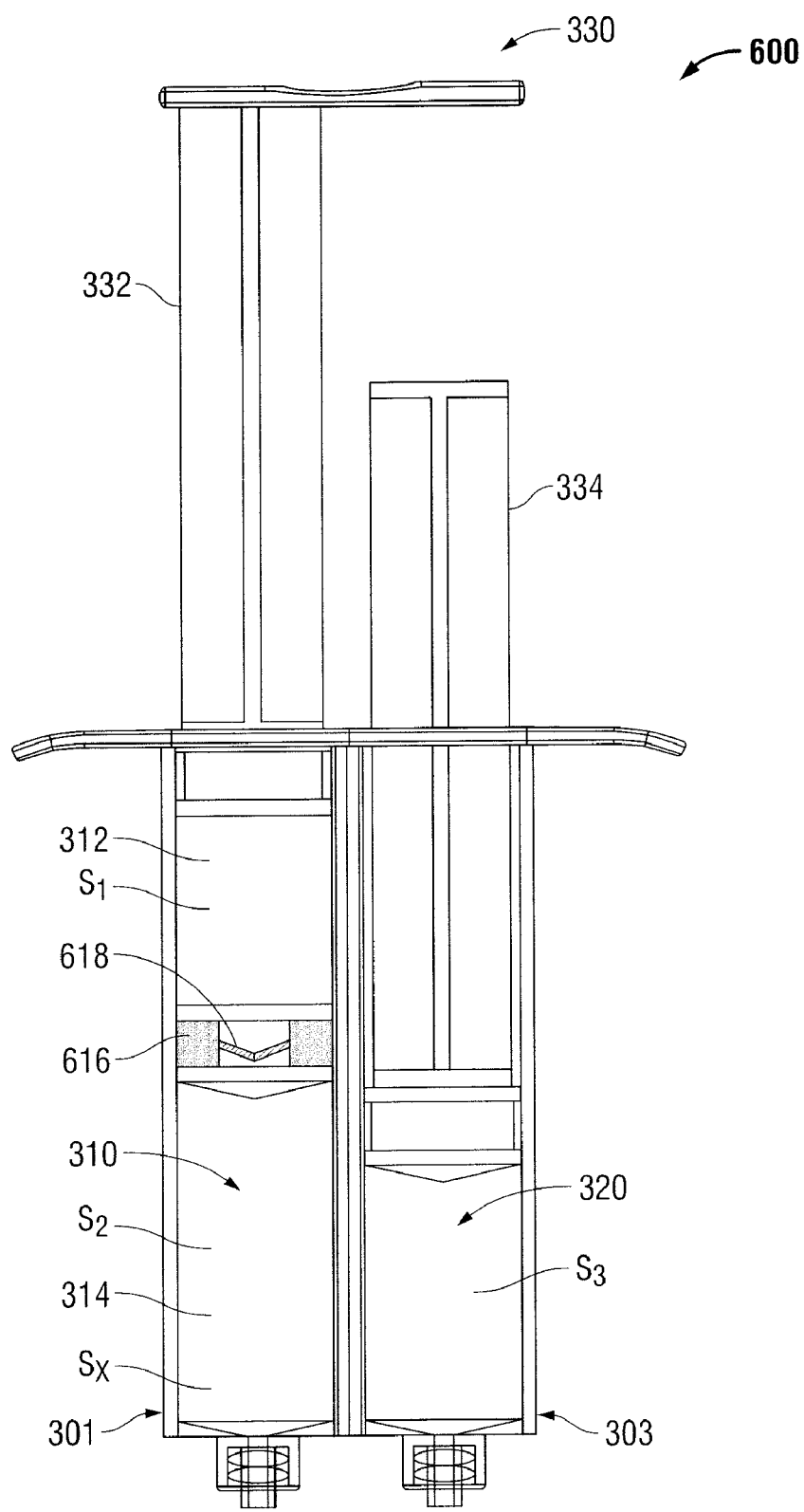
FIG. 9 is a front view of another embodiment of a syringe illustrating an internal stopper and a bypass in cross-section.

Illustrated in FIG. 9 is a syringe 600 that is substantially similar to syringe 500. However, syringe 600 includes an internal stopper 616 having a bypass 618 centrally disposed therein. In this embodiment, the bypass 618 is a one way check valve disposed in mechanical cooperation with the internal stopper 616 about the longitudinal axis thereof. In operation, the first member 332 of the plunger 330 is depressed, or otherwise advanced until applied pressure causes the check valve 618 to open, allowing the first substance S1 to advance through the check valve 618 and into the second chamber 314 of the first fluid conduit 310 before the internal stopper 616 is advanced, leaving no particulate. Although this embodiment is illustrated in a double barrel configuration, it is within the scope of the present disclosure that the check valve disposed in mechanical cooperation with the internal stopper may also be configured for use in a single barrel configuration or other multiple barrel configurations.

Figure 10:
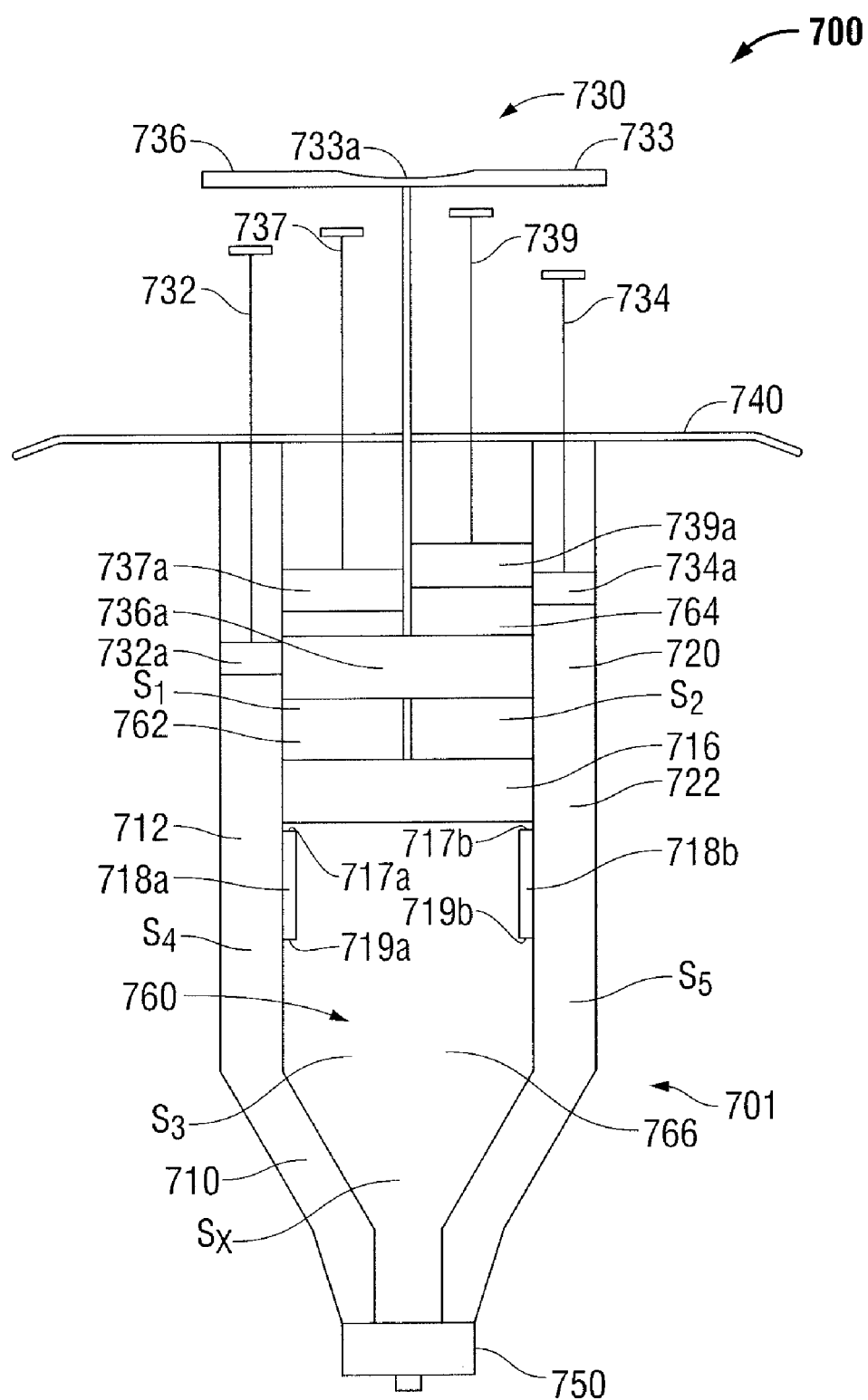
FIG. 10 is a front cross-sectional view of a further embodiment of a syringe in accordance with the present disclosure.

Referring now to FIG. 10, a syringe 700 is illustrated. Syringe 700 includes a unitary barrel 701 having a first fluid conduit 710, a second fluid conduit 720, and a third fluid conduit 760 disposed therein. The syringe 700 further includes a plunger 730 having first, second, third, fourth, and fifth members 732, 734, 736, 737, 739. The syringe 700 also includes a finger grip 740 and a discharge tip 750. Each fluid conduit 710, 720, 760 is disposed within the barrel 701 and in fluid communication with the discharge tip 750.

With continued reference to FIG. 10, the first fluid conduit 710 and the second fluid conduit 720 are disposed adjacent the third fluid conduit 760 on opposing sides thereof. The first fluid conduit 710 has one or more chambers 712 and the second fluid conduit 720 has one or more chambers 722 for accommodating one or more substances S4, S5, e.g., a fluid precursor, polymer, etc. The third fluid conduit 760 includes first, second, and third chambers 762, 764, 766. Each chamber 762, 764, 766 is configured to accommodate one or more substances in a hermetically sealed environment. For example, the first chamber 762 may accommodate a first substance S1, e.g., a fluid precursor (typically a liquid substance), and the second chamber 764 may accommodate a second substance S2, which may be the same or a different fluid precursor or mixture. The third chamber 766 may accommodate a third substance S3. For example, the third substance S3 may be a polymer (typically a powder substance) for intermixing with the first and second substances S1, S2 of the first and second chambers 762, 764 of the third fluid conduit 760. The syringe 700 includes a first bypass 718a and a second bypass 718b for enabling the first and second substances S1, S2 of the first and second chambers 762, 764 of the third fluid conduit 760 to intermix with the third substance S3 of the third chamber 766 of the third fluid conduit 760 when the first member 732 of plunger 730 is depressed or otherwise advanced to a predetermined point. The predetermined point is defined by where an internal stopper 716 exposes first bypass openings 717a, 717b of first and second bypasses 718a, 718b to enable the respective first and second substances S1, S2 to pass through the respective bypasses 718a, 718b and out second bypass openings 719a, 719b, and into the third chamber 766 of the third fluid conduit 760. However, the internal stopper of this embodiment may also be configured with a check valve or pressure filtration membrane as described above.

As illustrated in FIG. 10, the first member 732 of the plunger 730 is disposed at the proximal end of the first fluid conduit 710, the second member 734 of the plunger 730 is disposed at the proximal end of the second fluid conduit 720, the third member 736 of the plunger 730 is disposed at the proximal end of the third fluid conduit 760, the fourth member 737 is disposed at the proximal end of the first chamber 762 of the third fluid conduit 760, and the fifth member 739 is disposed at the proximal end of the second chamber 764 of the third fluid conduit 760 of the barrel 701. Each member 732, 734, 736, 737, 739 has a respective member head 732a, 734a, 736a, 737a, 739a. The first member 732 is operably associated with the first fluid conduit 710, the second member 734 is operably associated with the second fluid conduit 720, and the third, fourth, and fifth members 736 are operably associated with the third fluid conduit 760. The third member 736 includes a flange 733 having a thumb pad 733a. The flange 733 is configured and dimensioned to engage the first and second member 732, 734. The thumb pad 733a is configured for further facilitating a user's grip of the plunger 730. Each of the members 732, 734, 736, 737, 739 may be configured and dimensioned to interlock.

In operation, the third, fourth, and fifth members 736, 737, 739 of the plunger 730 are depressed, or otherwise advanced until the applied pressure causes the substances S1, S2 in the first and second chambers 762, 764 of the third fluid conduit 760 to advance the internal stopper 716 to a position adjacent the first and second bypasses 718a, 718b such that the flange 733 of the third member 736 engages the proximal end of the first and second members 732, 734. In this position, a predetermined volume of the substances S1, S2 in the first and second chambers 762, 764 of the third fluid conduit 760 may bypass the internal stopper 716 and advance through the bypasses 718a, 718b such that a predetermined volume of the each of the substances of first, second and third chambers 732, 734, 736 of the third fluid conduit 760 may intermix. The syringe 700 is then shaken to further facilitate the reconstitution of the substances disposed within the third fluid conduit 760, forming a predetermined volume of a third fluid conduit substance SX. First, second, and third members 732, 734, 736 of the plunger 730 may then be collectively depressed, causing the substance from each fluid conduit 710, 720, 760 to discharge from the discharge tip 750 disposed at the distal end of the barrel 701 and out a compatible spray tip ST (FIG. 11) that may be coupled thereto. The discharge tip 750 may be dimensioned for a threaded ISO 594 luer fitting for mating with an existing spray tip ST with a standardized luer hook-up. Alternatively, the discharge tip 750 may be dimensioned for a custom luer fitting such that distal end of the discharge tip 750 has wider dimensions for enabling easier distal loading. (However, this requires a custom spray tip with a compatible luer hook-up). As a result, a discharge material is formed for external application, e.g., through the discharge tip 750 and/or spray tip ST, from the combination of the substances. The discharge material may be defined by the intermixed composition of predetermined volumes of two or more substances of the fluid conduits 710, 720, 760. The resulting discharge material may be a hydrogel.

Referring now to FIG. 11, another embodiment of a syringe 800 is illustrated. Syringe 800 is substantially similar to syringe 300. However, in this embodiment, the syringe 800 further includes a third fluid conduit 860 partially disposed in a third barrel 805 and partially disposed in a third discharge tip 350c. The third discharge tip 350c is disposed at the distal end of the third barrel 805. Similarly to discharge tips 350a, 350b, discharge tip 350c may be dimensioned for a threaded ISO 594 luer fitting for mating with an existing spray tip ST with a standardized luer hook-up. Alternatively, discharge tip 350c may be dimensioned for a custom luer fitting such that distal end has wider dimensions for enabling easier distal loading. (However, this requires a custom spray tip with a compatible luer hook-up). The syringe 800 further includes a plunger 830 having a first member 832 with a first member head 832a, a second member 334 with a second member head 334a, and a third member 836 with a third member head 836a. The syringe 800 also includes a finger grip 840 disposed at the distal end.

With continued reference to FIG. 11, the third fluid conduit 860 is substantially similar to the second fluid conduit 320. The third fluid conduit 860 is disposed in the third barrel 805 adjacent the first barrel 301 and has one or more chambers 822 for accommodating one or more substances, e.g., a third fluid precursor. Furthermore, the third discharge tip 350c is disposed at the distal end of the third barrel 805.

As illustrated in FIG. 11, the first member 832 of the plunger 830 is disposed at the proximal end of the first fluid conduit 310 (and first barrel 301) and the second member 334 is disposed at the proximal end of the second fluid conduit 320 (and second barrel 303). Similarly, the third member 836 of the plunger 830 is disposed at the proximal end of the third fluid conduit 860 (and third barrel 805).

Referring additionally to FIG. 11, the first member 832 is substantially similar to first member 332 of syringe 300, however, first member 832 includes a flange 833 that extends distally away from the longitudinal axis of the first member 832 and is configured and dimensioned to engage the second member 334 and the third member 836. In addition, the flange 833 includes a thumb pad 833a for further facilitating a user's grip of the plunger 830. The first, second, and third members 832, 334, 836 of the plunger 830 may be configured and dimensioned to interlock.

With continued reference to FIG. 11, the syringe 800 may further include a connecting tip 870 for removably attaching to the discharge tips 350a, 350b, 350c. As illustrated in FIG. 11, the connecting tip 870 has a body 872 including a first branch 474, a second branch 476 and a third branch 878 disposed on the proximal end thereof. The body 872 includes first, second, and third fluid passages 873, 874, 875 disposed in fluid communication with the respective first, second, and third discharge tips 350a, 350b, 350c and the spray tip ST. Each branch 474, 476, 878 is removably attachable to each respective discharge tip 350a, 350b, 350c. The distal end may be configured to mechanically cooperate with a spray tip ST for the external application of the discharge material, e.g., hydrogel.

In operation, the first member 832 of the plunger 830 is depressed, or otherwise advanced until the applied pressure causes the first substance S1 to advance the internal stopper 316 within the first barrel 301 to a position adjacent the bypass 318 such that the flange 833 of the first member 832 engages the proximal end of the second member 334 and the third member 836. In this position, a predetermined volume of the first substance S1 may bypass the internal stopper 316 and advance through the bypass 318 such that a predetermined volume of the first substance S1 and a predetermined volume of the second substance S2 of the first fluid conduit 310 may interact. The syringe 800 is then shaken to further facilitate the reconstitution of the first substance and the second substance S1, S2 of the first fluid conduit 310, forming a predetermined volume of a first fluid conduit substance SX. Upon further simultaneous depression upon each respective member 832, 334, 836 of the plunger 830, the first member 832 causes the first fluid conduit substance SX to advance through the first fluid conduit 310, the second member 334 causes one or more substances S3 of the second fluid conduit 320 to advance therethrough, and the third member 836 causes one or more substances S4 of the third fluid conduit 860 to advance therethrough. Each substance is intermixable to form a discharge material (not shown) for external application upon advancement of the plunger 830 operably associated with each fluid conduit 320, 330, 860. As a result, a discharge material is formed for external application, e.g., through the discharge tips 350a, 350b, 350c from the combination of the substances. The discharge material may be defined by the intermixed composition of predetermined volumes of two or more substances of the fluid conduits 310, 320, 860. The resulting discharge material may be a hydrogel.

Figure 12:
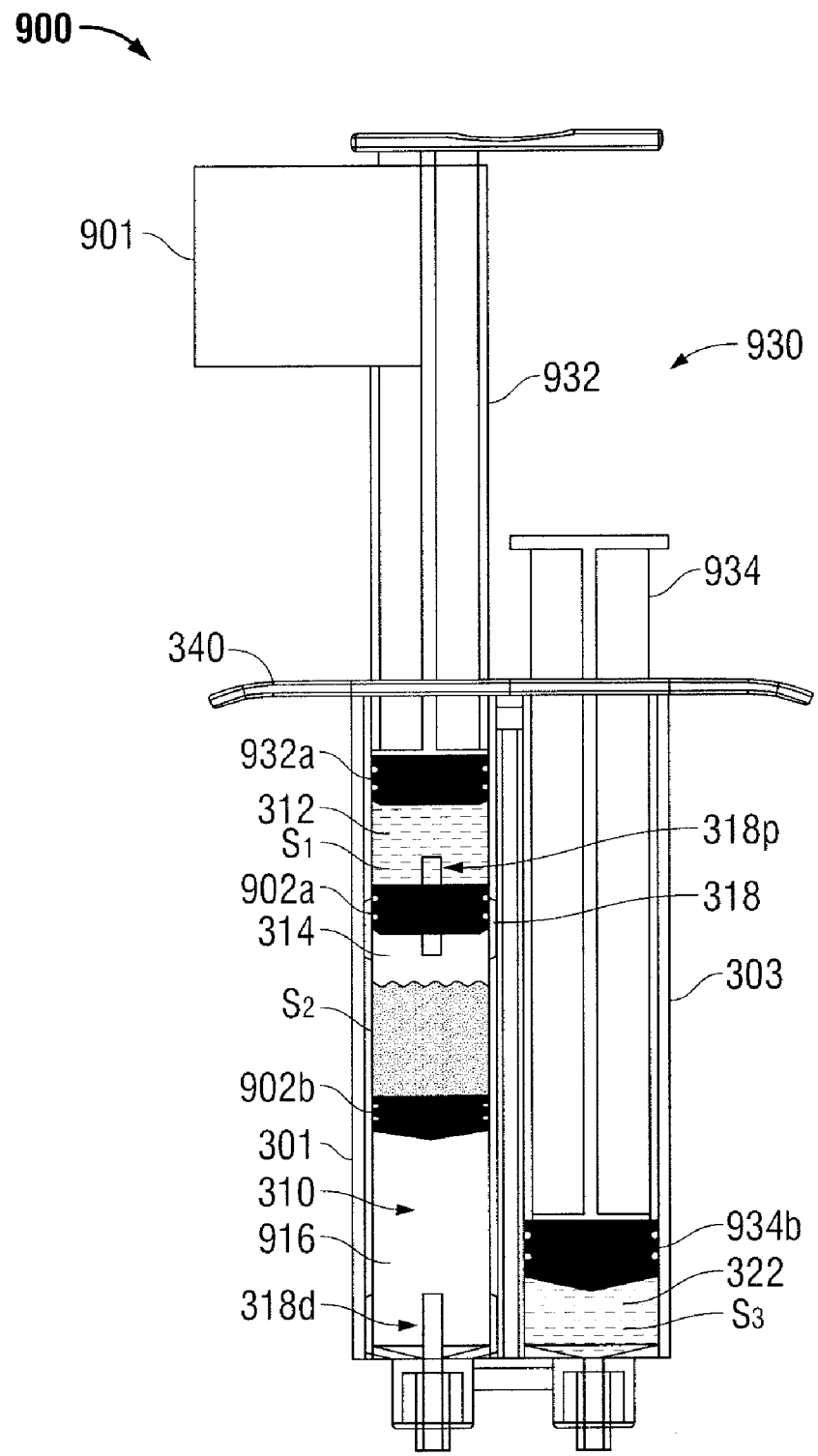
FIG. 12 is a front view of yet another embodiment of a syringe shown in one position.

Referring now to FIG. 12, another embodiment of a syringe 900 is illustrated. Syringe 900 is substantially similar to syringe 300. However, in this embodiment, the syringe 900 includes both a stop mechanism 901 and a second, more distal set of bypass channels 318d. The stop mechanism 901 is mounted to a plunger 930 for preventing further advancement of the plunger 930 when the plunger 930 is advanced to a predetermined point. The plunger 930 has a first member 932 (e.g., a non conventional plunger) and a second member 934 (e.g., a conventional plunger). Each of the first and second members 932, 934 include a head 932a, 934b. As illustrated in FIG. 12, each head 932a, 934b may be substantially accordion shaped. The second set of bypass channels 318d allow for fluid flow of the second substance 52 around stopper 902b once second substance 52 is adequately mixed in chamber 314.

With continued reference to FIG. 12, the first fluid conduit 310 includes a first chamber 312, a second chamber 314, and a third chamber 916. The first and second chambers 312, 314 are separated by a substantially cylindrically shaped accordion stopper 902a. Similarly, the second and third chambers 314, 916 are separated by a substantially frustoconically shaped accordion stopper 902b. The barrel 301 may include two or more bypasses 318 which may be disposed at a plurality of longitudinal and/or radial positions along and/or around the barrel 301. For example, the barrel 301 may include proximal bypasses 318p (FIG. 13A) radially disposed around the barrel 301 at a first longitudinal position between first and second chambers 312, 314. Referring again to FIG. 13A, the barrel 301 may similarly include distal bypasses 318d radially disposed at a second longitudinal position at the distal end of the barrel 301. As best shown in FIG. 13B, the proximal bypasses 318p may also be longitudinally offset from one another, such as bypass 318p' and 318p" for combining the first substance S1 with the second substance S2 at various flow rates. Each of these bypasses may be shaped (e.g., square, rectangle, triangle, etc.) and/or dimensioned (e.g., length, width, depth, etc.) to any suitable configuration in order to accommodate various substances or combinations of substances at one or more flow rates therethrough.

Figure 13A:
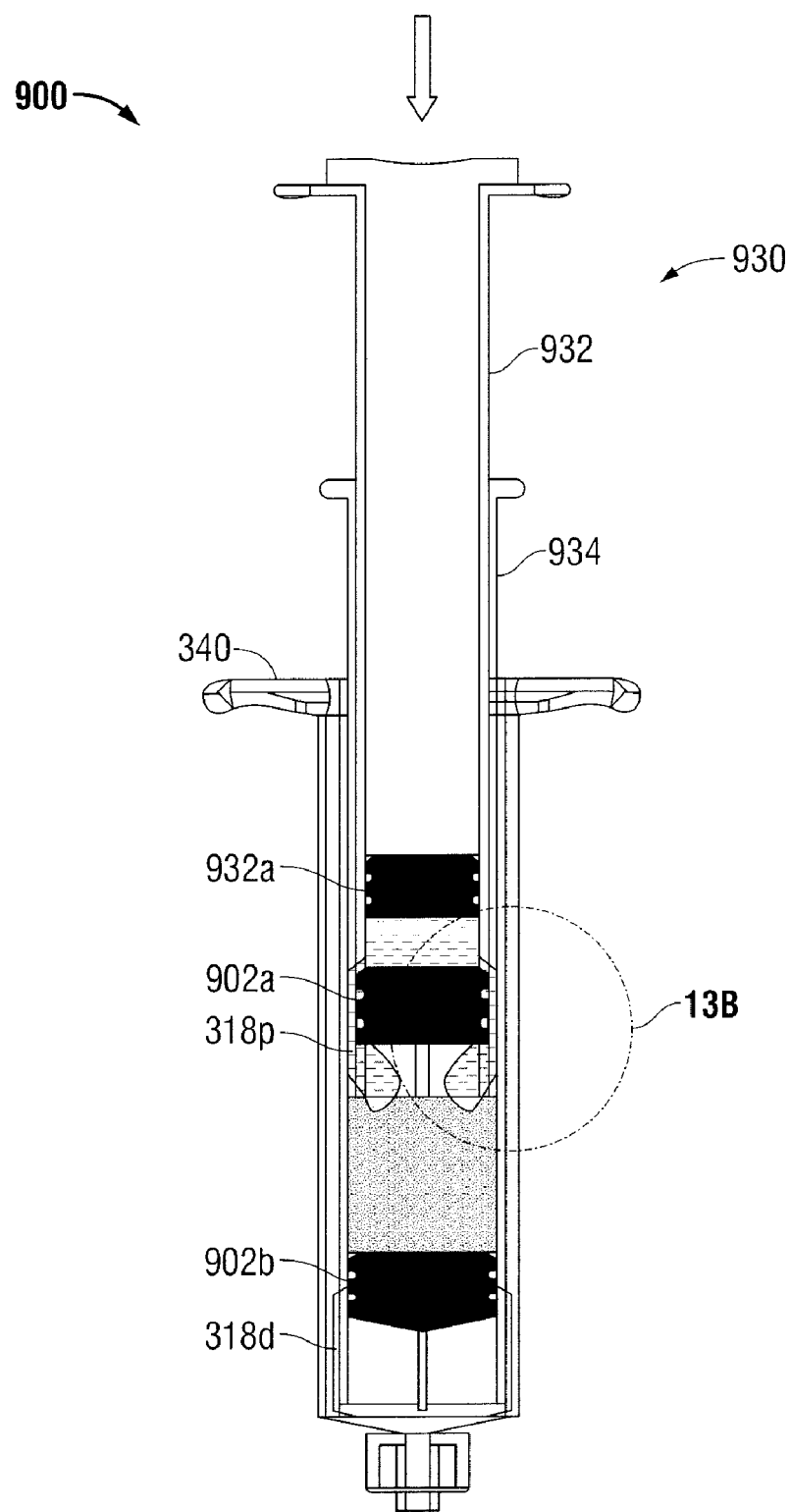
FIG. 13A is a side view of the syringe of FIG. 12 shown in another position.
Figure 13B:
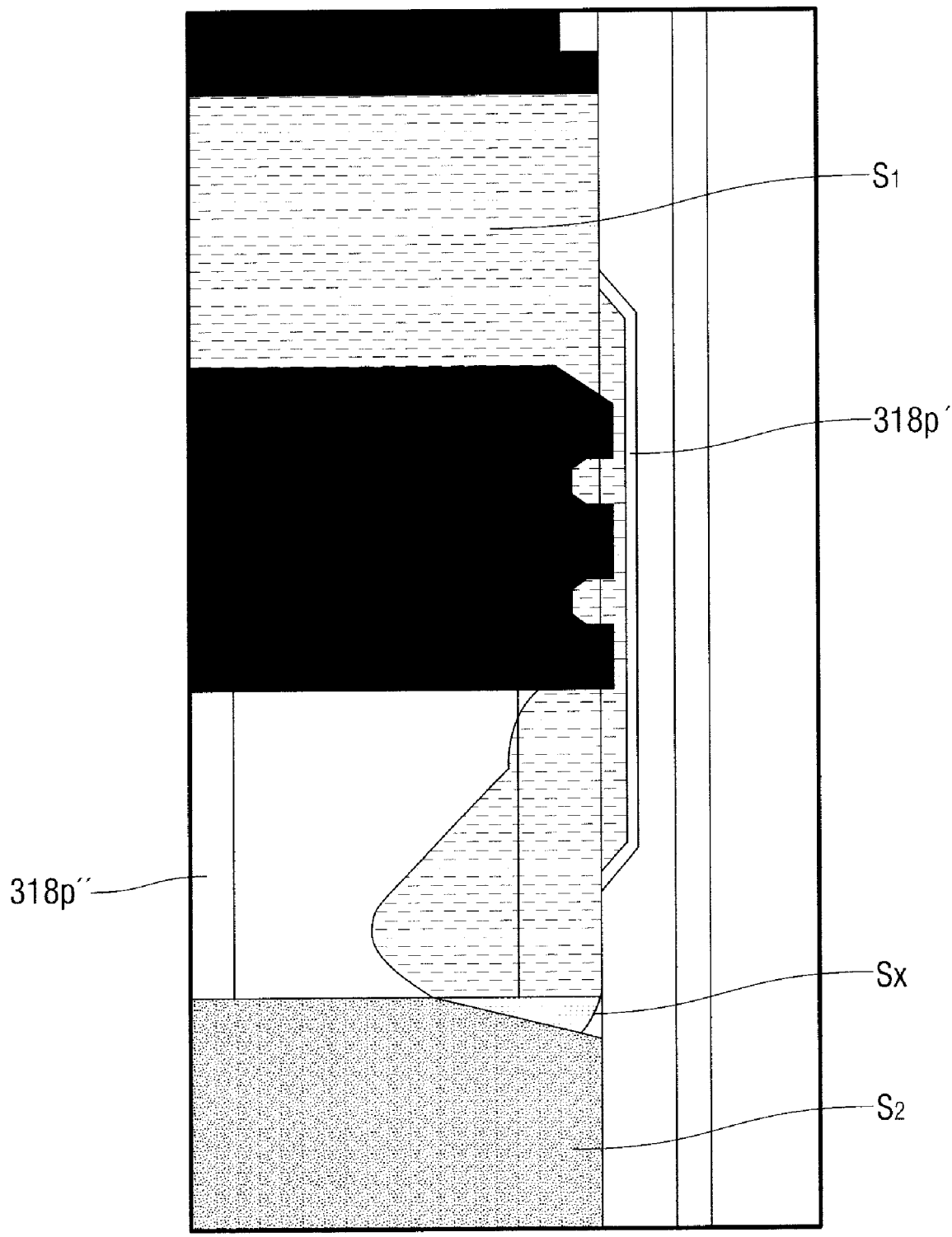
FIG. 13B is an enlarged view of the indicated area of detail shown in FIG. 13A.
Figure 14:
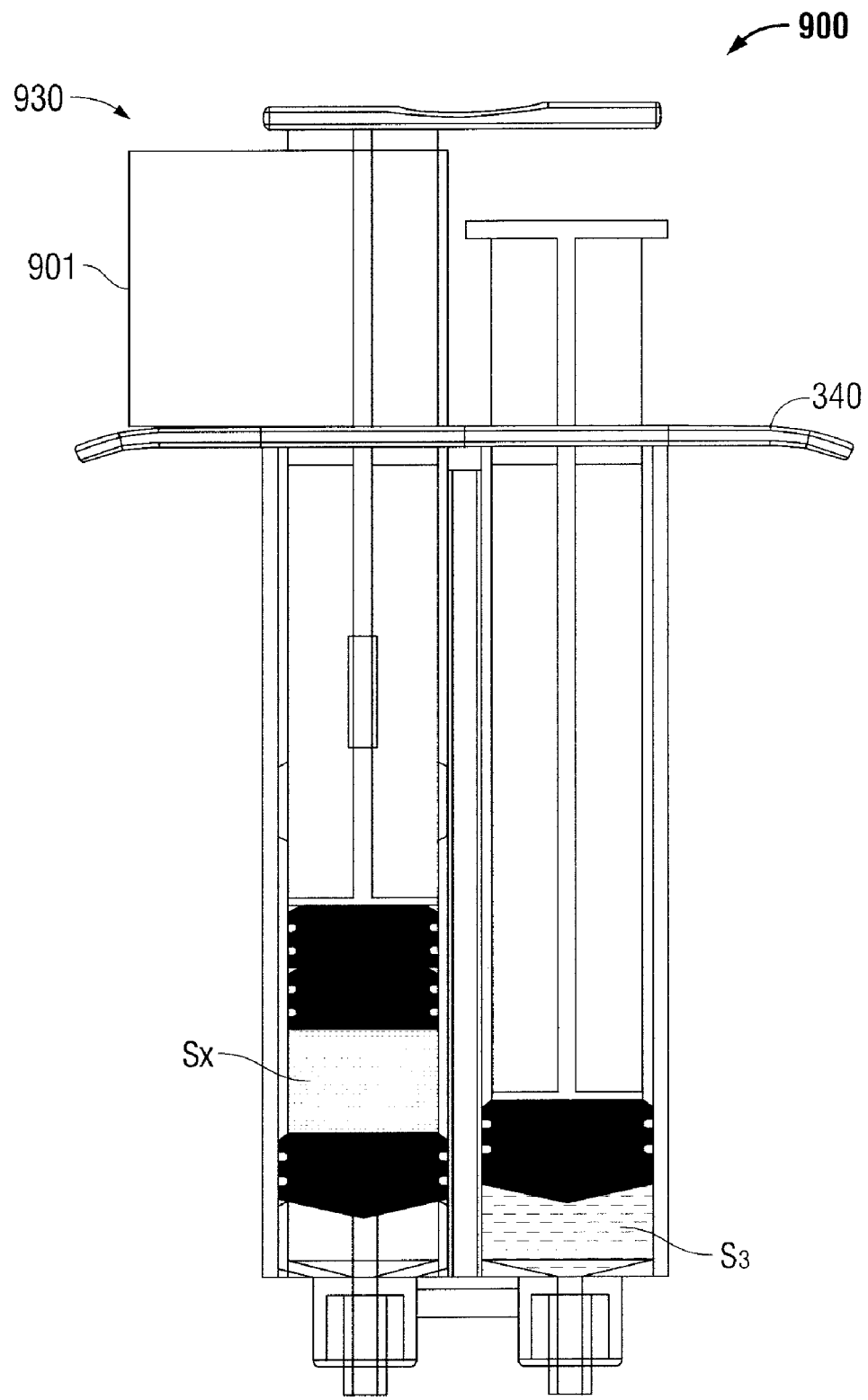
FIG. 14 is an enlarged front view of the syringe of FIG. 12 shown in yet another position.

In operation, the first member 932 of the plunger 930 is depressed, or otherwise advanced until the applied pressure from the head 932a causes the first substance 51 to advance stopper 902a so that the first substance S1 (e.g., a Phosphate Buffer Solution) passes from first chamber 312 through the one or more proximal bypasses 318p and intermixes with the second substance S2 (e.g., PEG powder) in the second chamber 314 (FIGS. 13A-13B). With particular reference to FIG. 13B, the first substance S1 will pass through the proximal-most bypasses 318p' first and upon being positioned to a predetermined location distal of the proximal-most bypasses 318p' will begin to pass through the one or more distal-most proximal bypasses 318p". In this manner, the head 932a approximates the stopper 902a as the first substance S1 passes through the one or more proximal bypasses 318p. With reference to FIG. 14, the stop mechanism 901 may be shaped and sized to prevent further distal advancement of the first member 932 of the plunger 930 when the first member 932 reaches a predetermined location such that a predetermined volume of the first substance S1 has been advanced from the first chamber 312 into the second chamber 314, but not into the third chamber 916.

Figure 15:
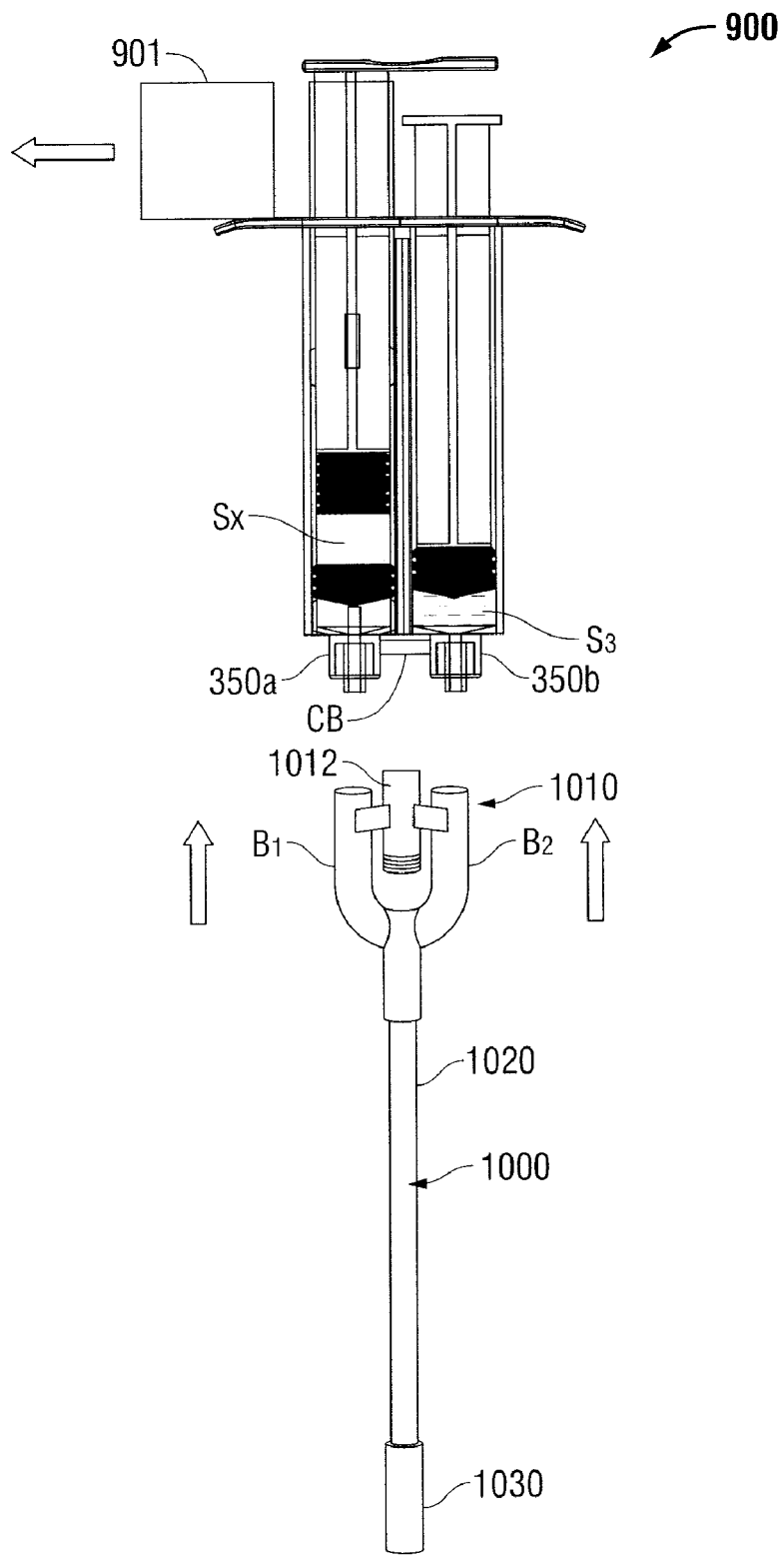
FIG. 15 is a front view of the syringe of FIG. 12 and an embodiment of a sprayer being shown mounted thereto, the syringe including a stop mechanism being removed therefrom.
Figure 17A:
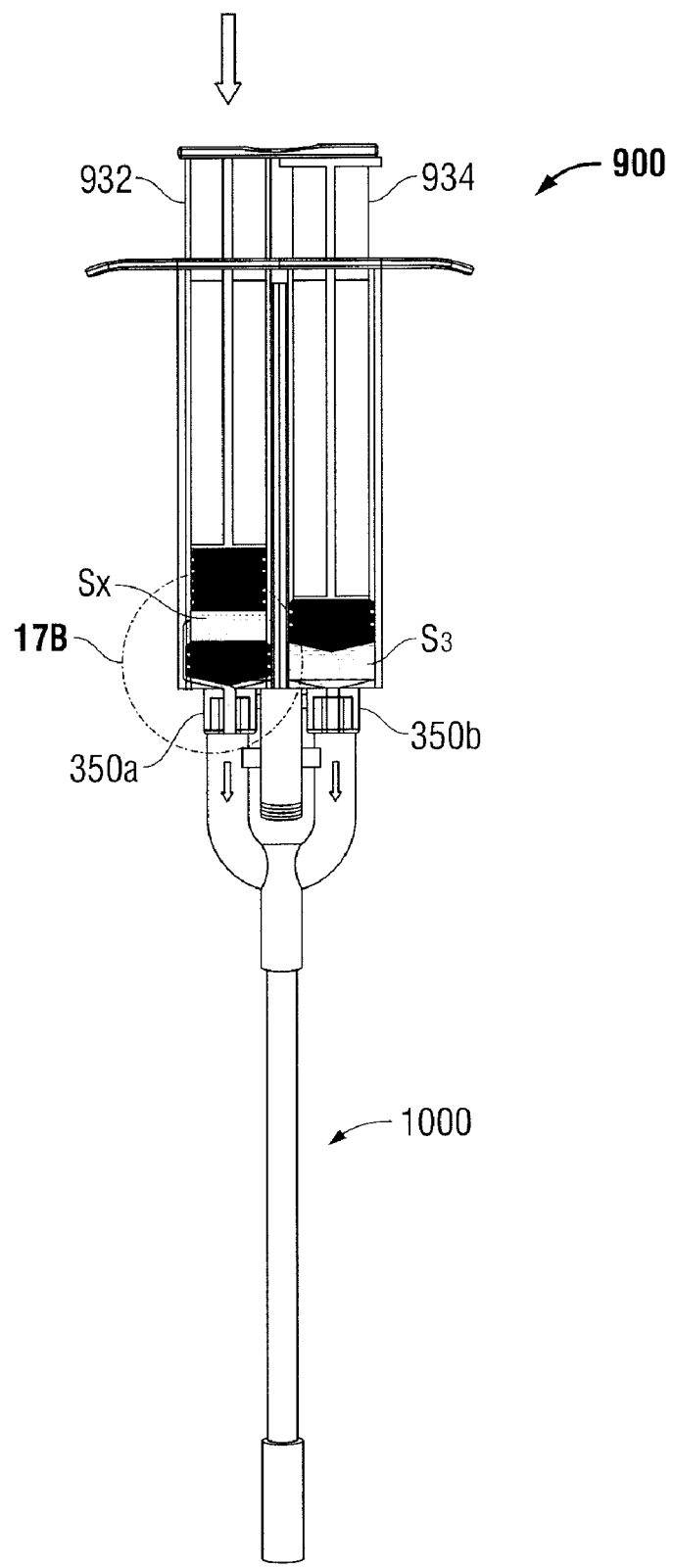
FIG. 17A is a front view of the syringe and sprayer with the syringe being shown in yet another position.
Figure 17B:
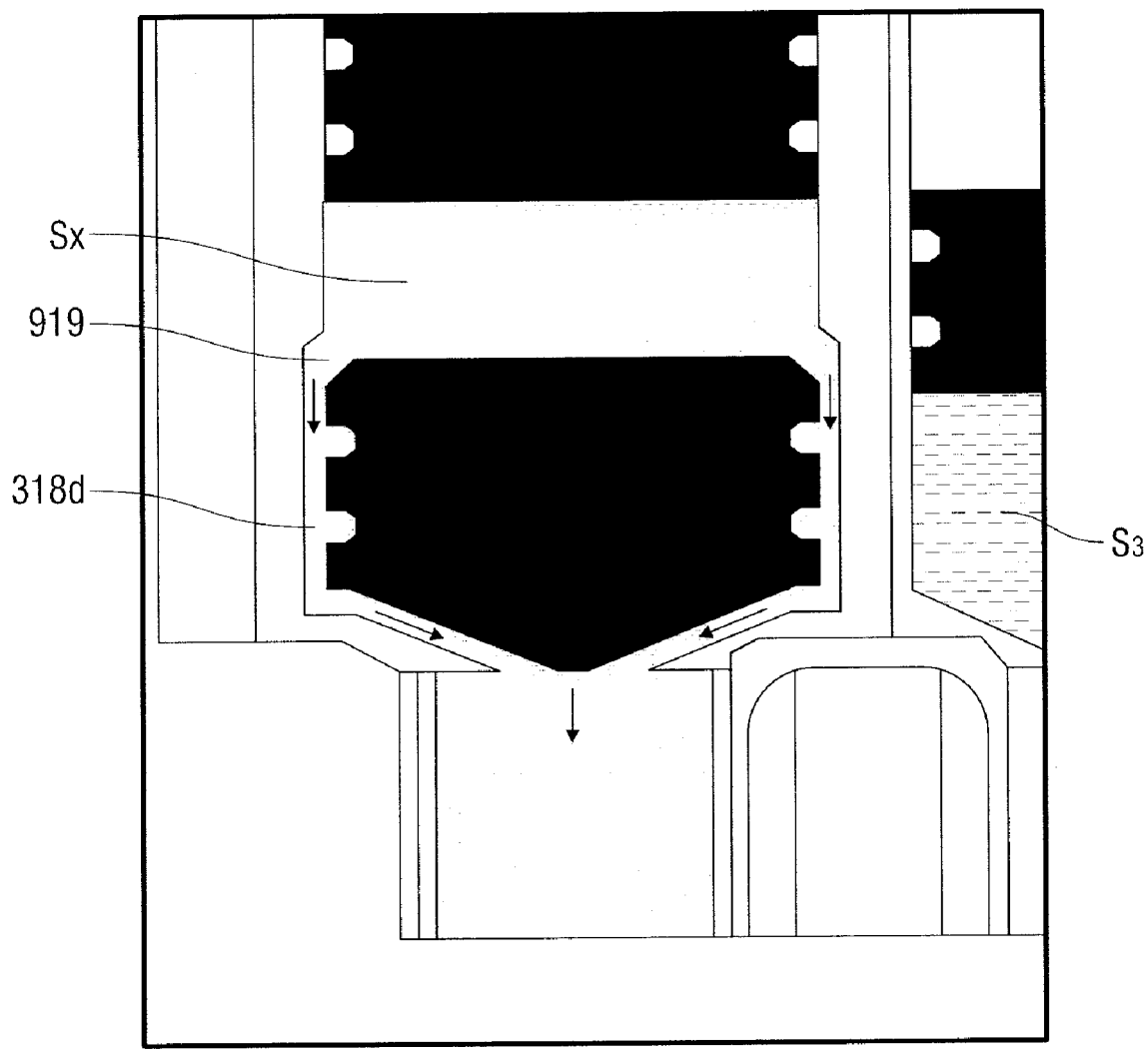
FIG. 17B is an enlarged view of the indicated area of detail shown in FIG. 17A.

As illustrated in FIG. 15, after positioning the first member 932 in the predetermined location, the clinician may shake syringe 900 to further facilitate the reconstitution of the first substance S1 and the second substance S2 of the first fluid conduit 310, forming a predetermined volume of a first fluid conduit substance SX (e.g., S1+S2). Thereafter, the clinician my remove stop mechanism 901. The first member 932 may then also be further distally advanced until the first member 932 contacts the second member 934 so that first and second members 932, 934 may be simultaneously advanced upon the depression thereof. In this manner, the depression of first member 932, the head 932a, stopper 902a, and substance SX advances stopper 902b to the distal end of the third chamber 916 so that proximal openings 919 (FIG. 17B) of the distal bypasses 318d are exposed. As such, distal bypasses 318d provide a passage through which substance SX may pass (FIG. 17A). In this respect, and as illustrated in FIG. 17A, substance SX is in fluid communication with the discharge tip 350a, substance S3 is in fluid communication with discharge tip 350b, and the first and second members 932, 934 are uniformly and simultaneously advanceable to uniformly and simultaneously dispense substance SX and substance S3 through the discharge tips 350a, 350b.

As shown in FIGS. 15-16, a spray applicator 1000 may be mounted to the discharge tips 350a, 350b for permitting the reception and passage of one or more substances (e.g., SX and S3) therethrough upon the advancement of the plunger 930 such that the one or more substances are intermixable to form a discharge material (not shown) for external application. As a result, a discharge material is formed for external application. The discharge material may be defined by the intermixed composition of predetermined volumes of substance SX and S3. The resulting discharge material may be a hydrogel.

Figure 16A:
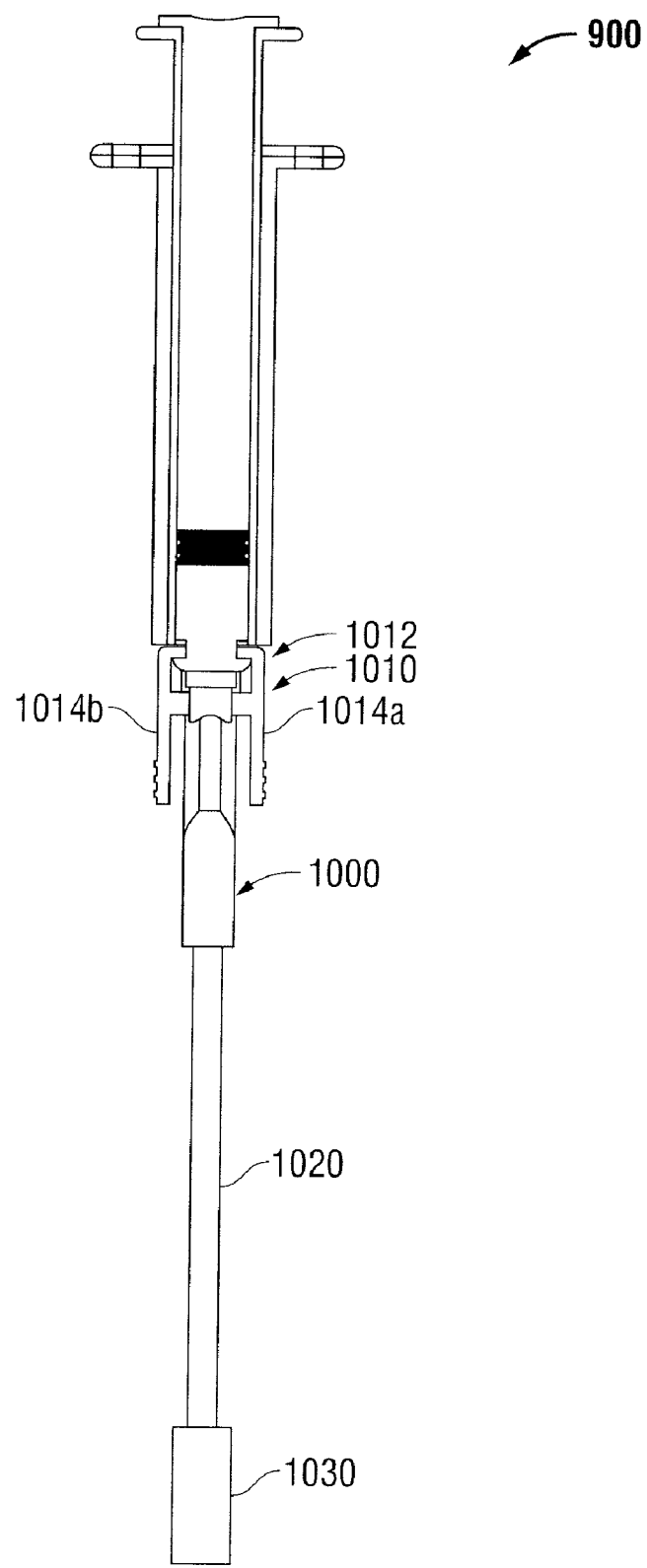
FIG. 16A is a side cross-sectional view of the sprayer and syringe with the sprayer shown mounted to the syringe.
Figure 16B:
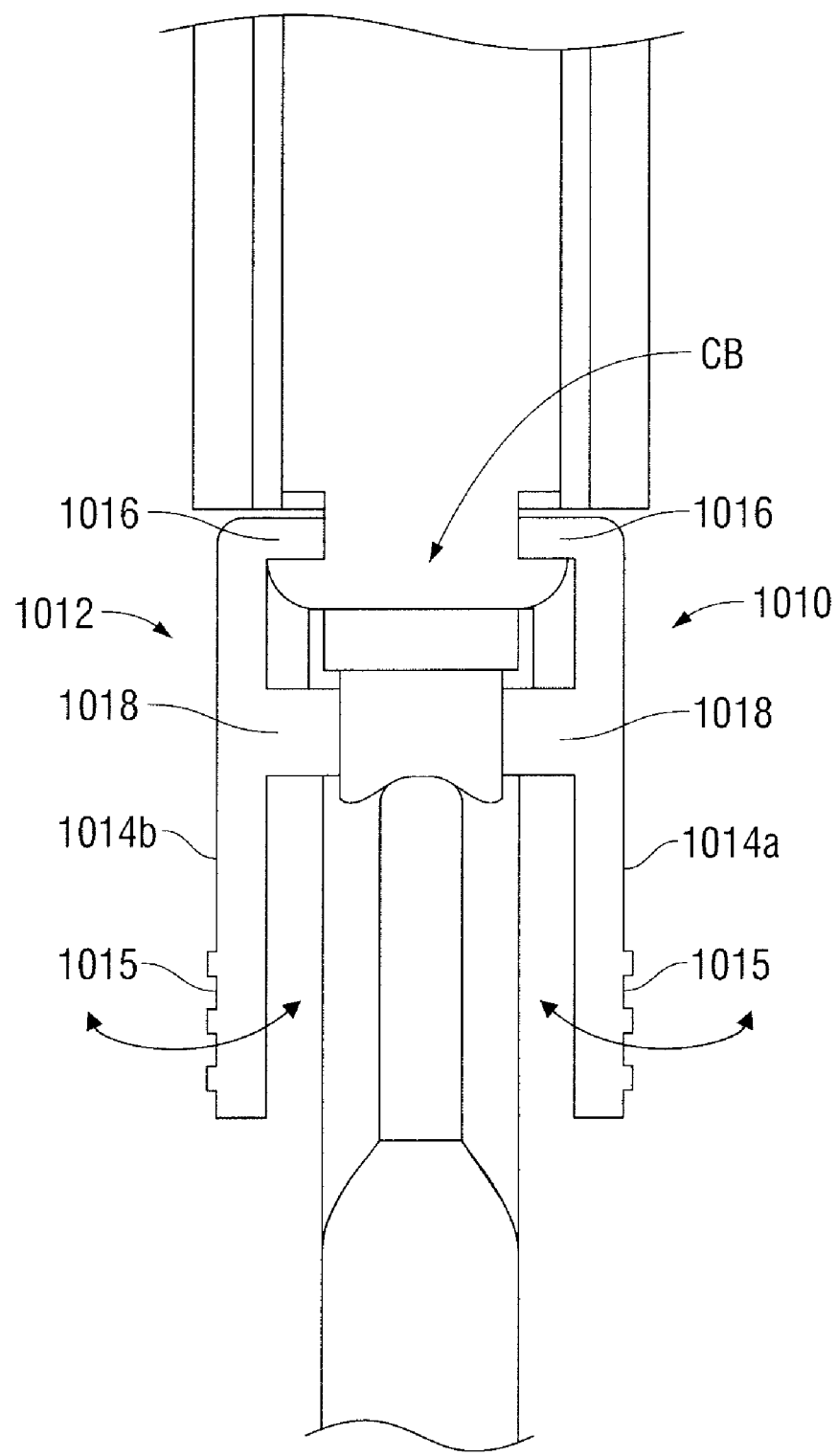
FIG. 16B is an enlarged view of a portion of the view shown in FIG. 16A.

With reference to FIGS. 15-16A, the spray applicator 1000 may include a connector assembly 1010, an elongate member 1020 extending from the connector assembly 1010, and a spray tip 1030 mounted to the distal end of the elongate member 1020. The connector assembly 1010 includes a coupler assembly 1012 for coupling the spray applicator 1000 to the syringe 900 and first and second branches B1, B2 (FIG. 15). The first and second branches B1, B2 are mechanically coupled to each of the discharge tips 350a, 350b via any suitable mechanical coupling such as pressure fit, snap fit, luer lock, threaded engagement, etc. From FIGS. 16A-16B, the coupler assembly 1012 includes opposing pivotable arms 1014a, 1014b (e.g., spring biased) having a latch mechanism 1016 extending therefrom for engagement with a cross bar CB extending from the syringe 900. The latch mechanisms 1016 may engage the cross bar CB for mounting the spray applicator 1000 to the syringe 900.

As best shown in FIG. 16B, each arm 1014a, 1014b is positioned to move between first and second positions. Each arm 1014a, 1014b may be biased towards the first position, which is in substantial alignment with the longitudinal axis of the syringe 900. The latch mechanisms 1016 of the arms 1014a, 1014b are outwardly pivotable about a pivot 1018 upon the application of force to release pads 1015 positioned at the distal ends of the arms 1014a, 1014b so that the latch mechanisms 1016 disengage from the cross bar CB for removing the spray applicator 1000 from the syringe 900. Upon release of force, the latch mechanisms pivot inwardly about the pivot 1018 and the release pads pivot outwardly about the pivot 1018 such that the arms 1014a, 1014b bias or otherwise move back into the first position.

In other embodiments within the scope of the present disclosure, the plunger may be configured such that a user may depress a first member to a predetermined point to intermix a plurality of substances wherein upon withdrawal of the first member, the first member may interlock with other adjacent members. In another embodiment, the plunger may be configured such that a withdrawing of one or more members may cause a plurality of substances to intermix. In yet other embodiments, the outer fluid conduits of single barrel or multiple barrel configurations may have a plurality of chambers and/or sub-chambers for intermixing a plurality of substances.

Figure 18:
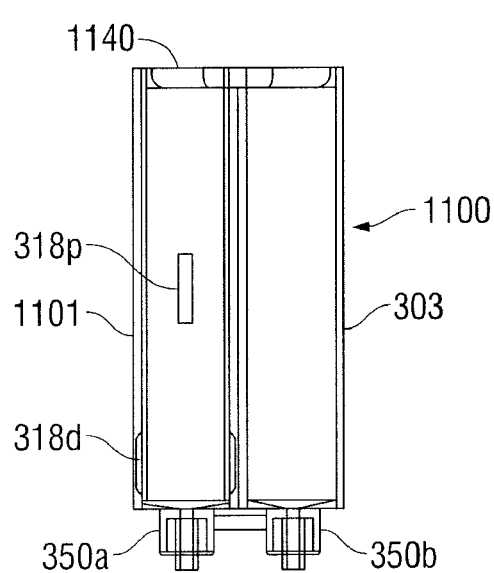
Figure 19:
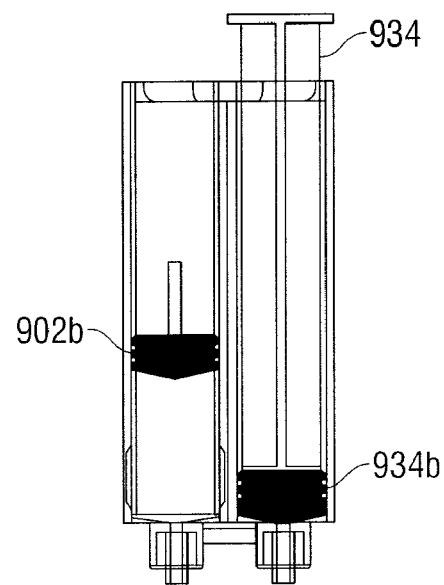
Figure 20:
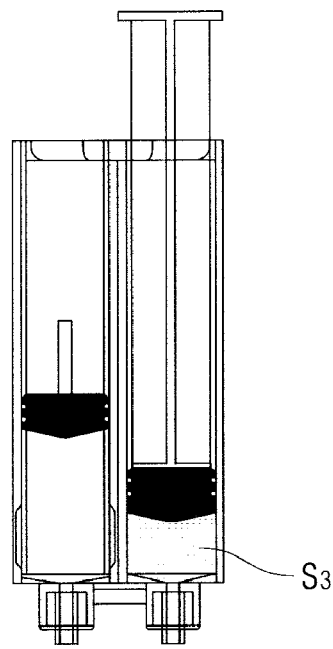
Figure 21:
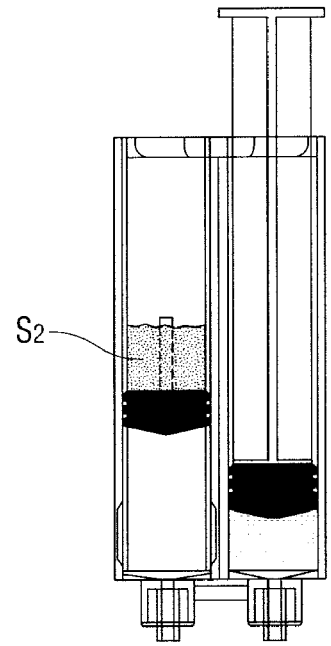

In one aspect, illustrated in progressive view 18-27B, a method of assembling a syringe 1100 includes providing an empty double-barrel construct having a first barrel 1101 with discharge tip 350a and a second barrel 303 with discharge tip 350b. The first and second barrels 1101, 303 are coupled by a handle 1140. As shown in FIG. 18, the first barrel 1101 includes one or more proximal bypasses 318p and one or more distal bypasses 318d. Referring to FIG. 19, a stopper 902b is then introduced into the first barrel 1101 adjacent the proximal bypass 318p and a second member (e.g., a conventional plunger) 934 having a head 934b is introduced into the second barrel 303. As illustrated in FIG. 20, a substance S3 (e.g., a borate buffer solution) is introduced into the second barrel 303 via a standard Luer-lock distal opening (e.g., to accommodate conventional distal end syringe loading). From FIG. 21, a substance S2 (e.g., PEG powder) is then introduced into the first barrel 1101 adjacent the one or more proximal bypasses 318p and the stopper 902b.

Figure 22B:
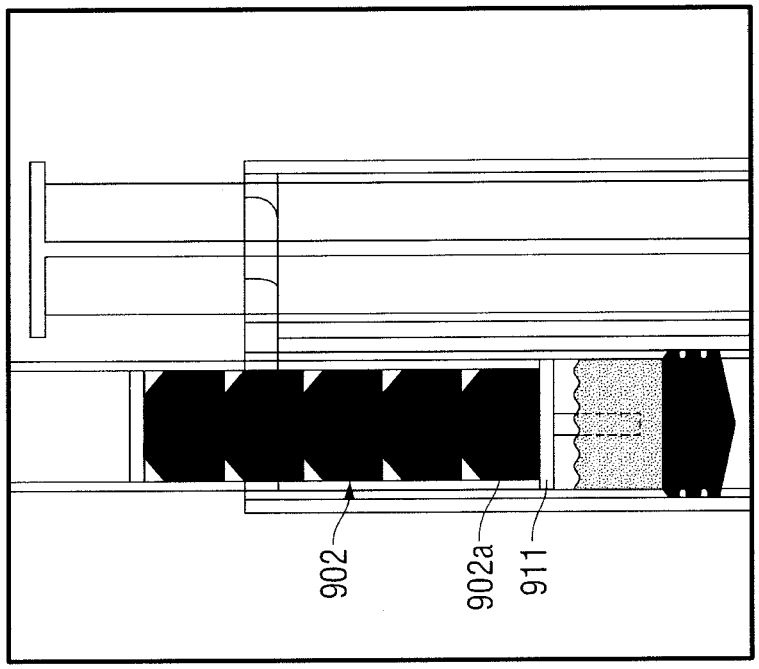
Figure 22A:
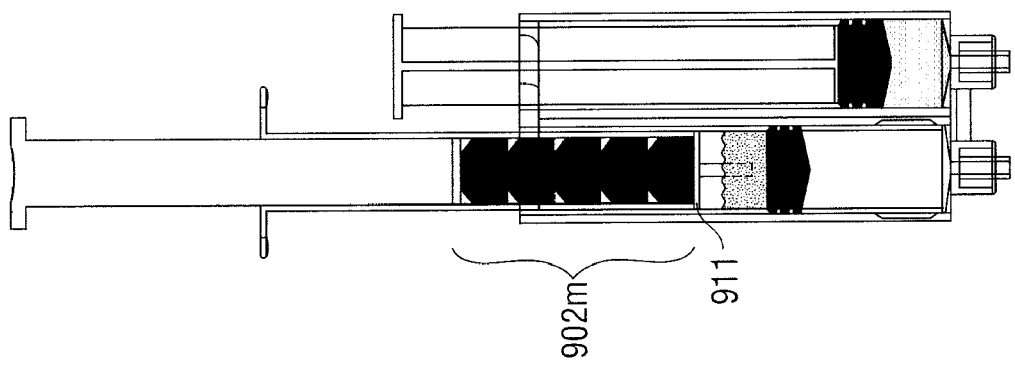
Figure 23B:
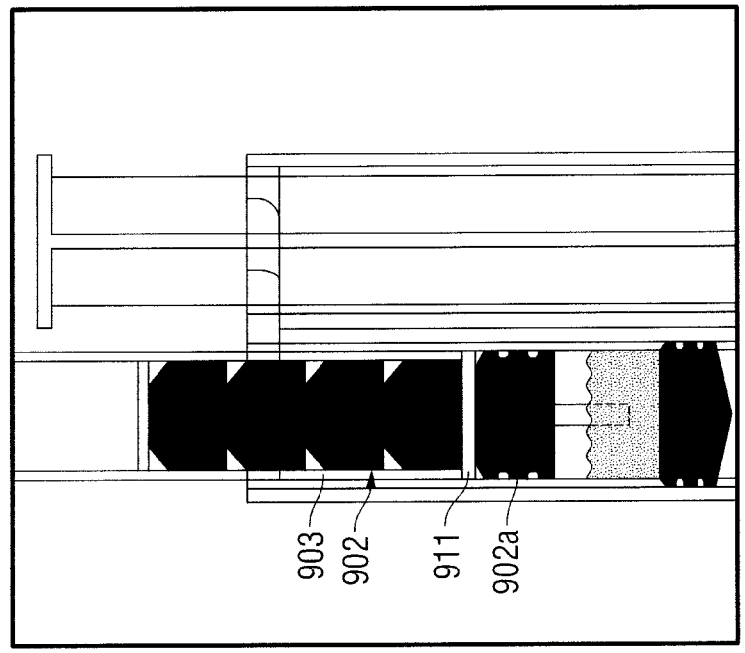
Figure 23A:
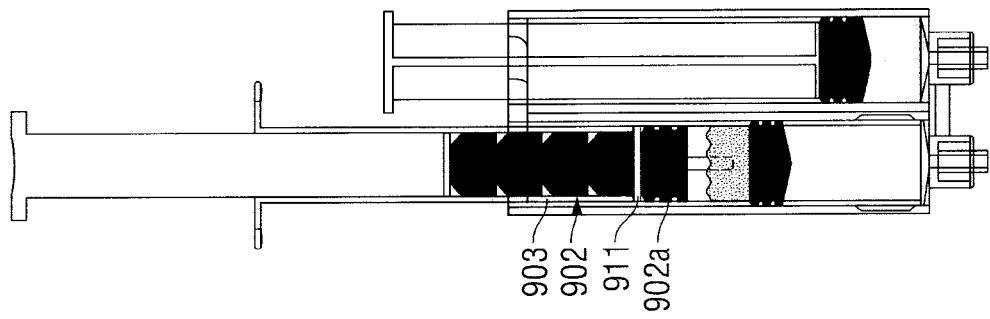

Referring now to FIGS. 22A and 22B, another step includes introducing a stopper loading device 902m into the first barrel 1101 adjacent substance S2. As best shown in FIG. 22B, the stopper loading device 902m includes a plurality of stoppers 902 loaded in a "magazine" fashion. Each of the stoppers 902 are positioned in a compressed condition. As illustrated in FIGS. 23A and 23B, a further step includes unloading the distal-most stopper 902a out of a sheath 903 of the stopper loading device 902m and into the first barrel 1101. In particular, the sheath 903 includes a distal passage 911 for permitting one or more stoppers to pass therethrough. The step includes depressing the loading device 902m with a nonconventional plunger 932 relative to the sheath 903 so that stopper 902a is dispensed from the sheath 903. In this manner, the stopper 902a is positioned in an expanded condition after being dispensed from the sheath 903. In particular, the stopper 902a decompresses upon unloading from the sheath 903 and opens into the expanded condition (e.g., like an umbrella) such that the stopper 902a is positioned in contact with the inner wall of the first barrel 1101.

Figure 24:
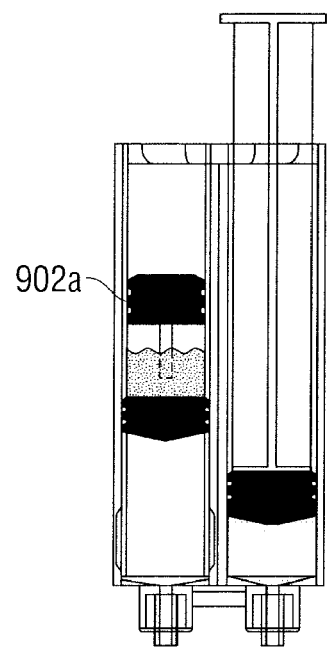
Figure 25:
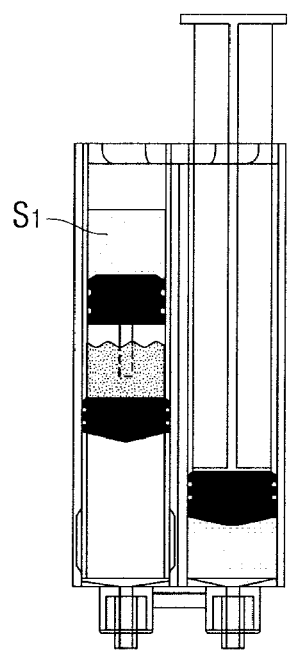

Referring now to FIG. 24, the stopper loading device 902m may then be removed with the stopper 902a remaining in the expanded condition within the first barrel 1101 adjacent substance S2. As shown in FIG. 25, a substance S1 (e.g., a phosphate buffer solution) is then introduced adjacent the stopper 902a. Referring now to FIGS. 26A and 26B, the first member (e.g. a non-conventional plunger) 932 which has a head 932a enclosed within a plunger sheath 904 and includes a stop mechanism 901 may then be introduced into the first barrel 1101. In this respect, the head 932a is loaded in the plunger sheath 904 similar to stoppers 902 in the stopper loading device 902m such that the head 932a is in a compressed condition.

Figure 27B:
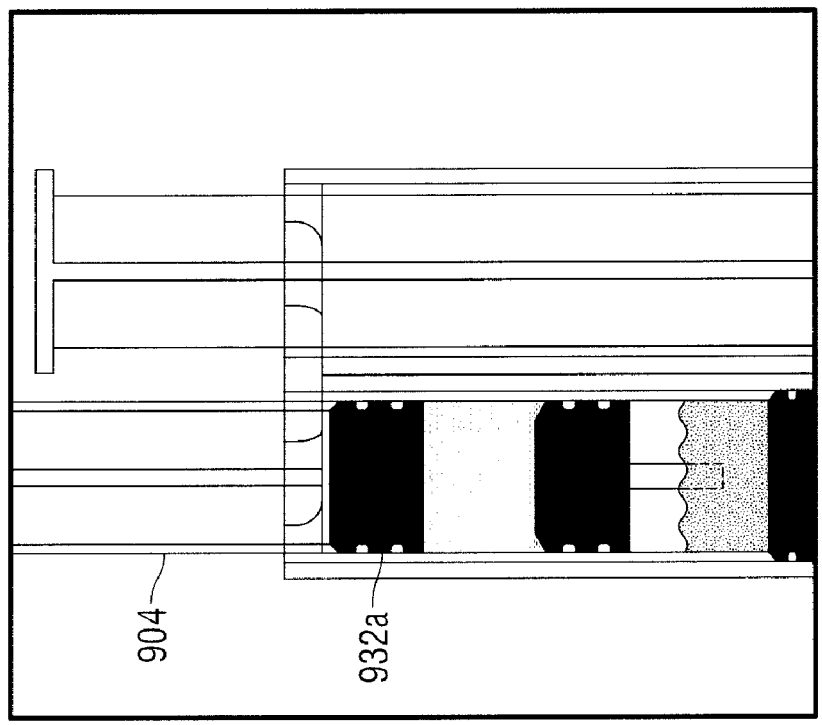
Figure 27A:
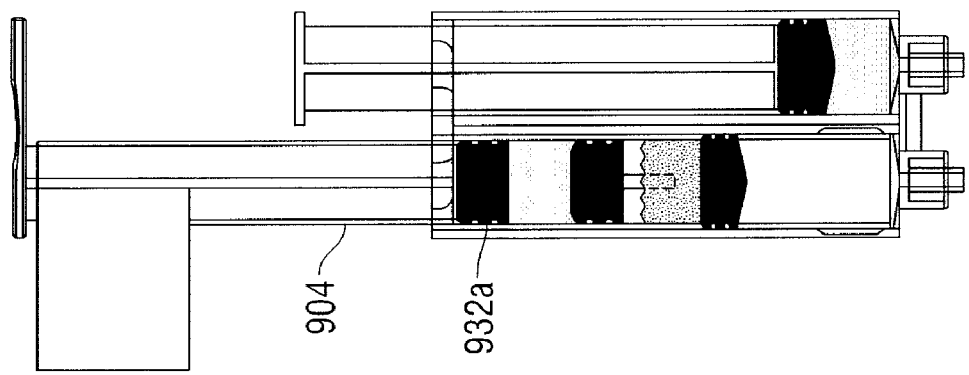

As illustrated in FIGS. 27A and 27B, the first member 932 may then be depressed by the nonconventional plunger 932 relative to the plunger sheath 904 so that the head 932a is dispensed from the plunger sheath 904. In this manner, the head 932a is positioned in an expanded condition after being dispensed from the plunger sheath 904. In particular, the head 932a decompresses upon unloading from the plunger sheath 904 and opens into an expanded condition (e.g., like an umbrella) to contact the inner wall of the first barrel 1101.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of the presently disclosed embodiments. Thus the scope of the embodiments should be determined by the appended claims and their legal equivalents, rather than by the examples given.

What is claimed is:

1. A syringe, comprising:
    a first fluid conduit having at least two chambers for accommodating at least two substances of a plurality of substances and at least two bypasses operably coupled to the at least two chambers for enabling the at least two substances of the first fluid conduit to intermix;
    a second fluid conduit disposed adjacent the first fluid conduit and having at least one chamber for accommodating at least one substance of the plurality of substances;
    each substance being intermixable to form a discharge material for external application upon advancement of a plunger operably associated with each fluid conduit, the discharge material defined by the intermixed composition of predetermined volumes of at least two substances of the fluid conduits; and
    an end cap disposed on the distal end of at least one of the fluid conduits, the end cap including at least one vent and a filter, the filter in fluid communication with the at least one vent for facilitating the passage of gas from the end cap, the at least one vent defined through a wall of the end cap, the filter being disposed within the end cap and spaced from the at least one vent.

2. A syringe according to claim 1, wherein the first fluid conduit accommodates a liquid substance in a first chamber and a powder substance in a second chamber, the liquid substance and the powder substance being intermixable to form a first fluid conduit substance.

3. A syringe according to claim 2, wherein the first fluid conduit substance and the at least one substance of the second fluid conduit define the discharge material upon intermixing thereof.

4. A syringe according to claim 1, wherein the discharge material is a hydrogel.

5. A syringe according to claim 1, further comprising at least one connecting tip operably associated with the distal end of at least one of each of the fluid conduits.

6. A syringe according to claim 5, wherein the connecting tip is configured and dimensioned to spray the discharge material to a surface disposed externally of the syringe.

7. A syringe according to claim 5, wherein the connecting tip is configured and dimensioned to accommodate the intermixing of at least two of the substances accommodated by the fluid conduits.

8. A syringe according to claim 1, wherein at least one chamber is hermetically sealed.

9. A syringe according to claim 1, wherein at least one chamber includes at least one internal stopper for separating at least two substances.

10. A syringe according to claim 9, wherein the at least one internal stopper is substantially accordion shaped.

11. A syringe according to claim 1, wherein the plunger further comprises at least one flange disposed at the proximal end of the plunger.

12. A syringe according to claim 1, wherein the plunger includes first and second members.

13. A syringe according to claim 12, wherein first and second members of the plunger are configured and dimensioned to interlock in order to facilitate the advancement of a predetermined volume of at least one substance and/or the discharge material.

14. A syringe according to claim 12, wherein each of the first and second members of the plunger are separately advanceable.

15. A syringe according to claim 12, wherein first and second members of the plunger are configured and dimensioned to simultaneously advance.

16. A syringe according to claim 1, wherein the plunger is configured and dimensioned to advance a predetermined volume of at least two of the substances.

17. A syringe according to claim 1, further comprising a third fluid conduit having at least one chamber for accommodating at least one substance of the plurality of substances.

18. A syringe according to claim 1, further comprising at least one stop mechanism removably coupled to the plunger that prevents the plunger from being advanced distally beyond a predetermined location.

19. A syringe according to claim 1, wherein the at least two bypasses includes a first bypass and a second bypass, the first bypass is longitudinally offset from the second bypass along a longitudinal axis of the first fluid conduit.

20. A syringe according to claim 19, wherein the first bypass is disposed proximally of the second bypass.

21. A syringe according to claim 1, wherein the at least two bypasses of the first fluid conduit are radially offset.

22. A syringe according to claim 21, wherein the at least two bypasses includes a first bypass and a second bypass, the first bypass is positioned transverse to the second bypass along the surface of the first fluid conduit.

23. A syringe according to claim 1, wherein the at least two chambers of the first fluid conduit are longitudinally offset along a longitudinal axis of the first fluid conduit.

* * * * *

UNITED STATES PATENT AND TRADEMARK OFFICE
CERTIFICATE OF CORRECTION

PATENT NO. : 8,376,989 B2
APPLICATION NO. : 12/721709
DATED : February 19, 2013
INVENTOR(S) : Rissman et al.

It is certified that error appears in the above-identified patent and that said Letters Patent is hereby corrected as shown below:

Title Page, Item (73) Assignee should read:

-- Confluent Surgical, Inc., Waltham, MA (US) --

Signed and Sealed this
Twenty-third Day of July, 2013

Teresa Stanek Rea
*Acting Director of the United States Patent and Trademark Office*